US008545683B2

(12) United States Patent
Tao et al.

(10) Patent No.: US 8,545,683 B2
(45) Date of Patent: Oct. 1, 2013

(54) SYSTEMS AND METHODS FOR INTEGRATED DETECTION

(75) Inventors: Nongjian Tao, Scottsdale, AZ (US); Erica Forzani, Mesa, AZ (US); Alvaro Diaz Aguilar, Tempe, AZ (US)

(73) Assignee: Arizona Board Of Regent For And On Behalf of Arizona State University, Scottsdale, AZ (US)

( * ) Notice: Subject to any disclaimer, the term of this patent is extended or adjusted under 35 U.S.C. 154(b) by 154 days.

(21) Appl. No.: 13/063,499

(22) PCT Filed: Sep. 11, 2009

(86) PCT No.: PCT/US2009/056655
§ 371 (c)(1),
(2), (4) Date: Sep. 11, 2009

(87) PCT Pub. No.: WO2010/030874
PCT Pub. Date: Mar. 18, 2010

(65) Prior Publication Data
US 2011/0266161 A1 Nov. 3, 2011

Related U.S. Application Data

(60) Provisional application No. 61/096,249, filed on Sep. 11, 2008.

(51) Int. Cl.
*G01N 27/416* (2006.01)
(52) U.S. Cl.
USPC ..................... 204/407; 205/793.5

(58) Field of Classification Search
USPC . 204/408, 407, 228.1–230.8; 205/775–794.5
See application file for complete search history.

(56) References Cited

U.S. PATENT DOCUMENTS

| 7,030,452 B2 | 4/2006 | Tao et al. |
| 2006/0214570 A1 | 9/2006 | Malliaras et al. |

FOREIGN PATENT DOCUMENTS

| WO | WO03/043541 A1 | 5/2003 |
| WO | WO2006040588 A1 | 4/2006 |
| WO | WO2007/138180 A1 | 6/2007 |
| WO | WO2008/110830 A1 | 9/2008 |

OTHER PUBLICATIONS

Aguilar, A. D., et al., "Chemical sensors using peptide-funcationalized conducting polymer nanojunction arrays", Applied Physics Letters, vol. 87, paper No. 193108, Nov. 7, 2005, 3 pages.*
Written Opinion of the International Search Authority, Mar. 11, 2011.
International Search Report, Mar. 18, 2010.
Tao et al. (2010) A Hybrid Nanosensor for TNT Vapor Detection. Nano Letters vol. 10 Issue: 2 pp. 380-384.

* cited by examiner

*Primary Examiner* — J. Christopher Ball
(74) *Attorney, Agent, or Firm* — George A. Leone; Citadel Patent Law

(57) ABSTRACT

An integrated sensor is capable of detecting analytes using electrochemical (EC), electrical (E), and optical (O) signals or EC and O signals. The sensor introduces synergetic new capabilities and enhances the sensitivity and selectivity for real-time detection of an analyte in complex matrices, including the presence of high concentration of interferences in liquids and in gas phases.

53 Claims, 21 Drawing Sheets

FIG. 2A
FIG. 2B
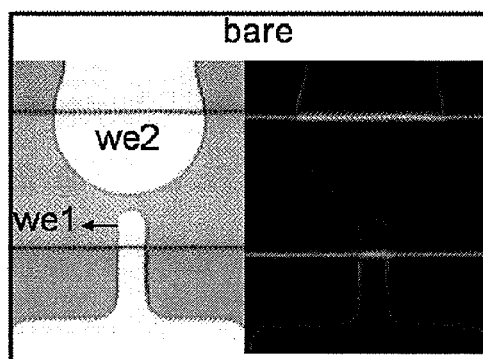
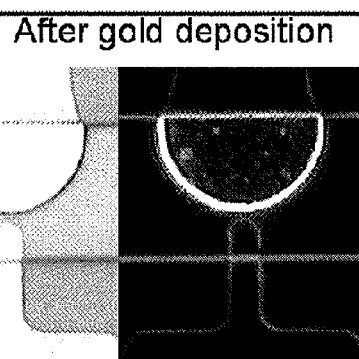
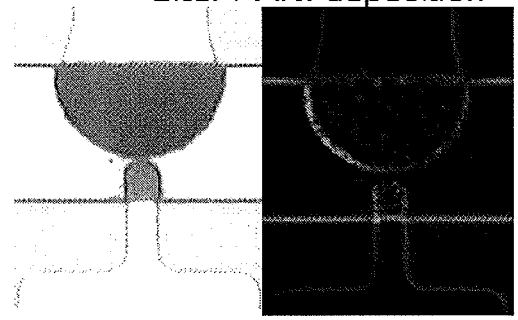
FIG. 2C

SYSTEMS AND METHODS FOR INTEGRATED DETECTION

CROSS-REFERENCE TO RELATED APPLICATIONS

This application claims priority to and incorporates by reference U.S. Provisional Patent Application Ser. No. 61/096,249 entitled, "Systems and Methods for Integrated Detection" which was filed on Sep. 11, 2008. This application also incorporates by reference U.S. Provisional Patent Application Ser. No. 60/939,738 entitled, "Systems and Methods for Integrated Electrochemical and Electrical Detection" which was filed on May 23, 2007.

BACKGROUND OF THE INVENTION

1. Field of the Invention

The present invention relates generally to sensors and, more particularly, to systems and methods for integrated electrochemical, electrical and/or optical detection.

2. Description of Related Art

Electrochemical sensors have been used in various chemical and medical applications to detect concentrations of biological analyte. However, the inventors hereof have recognized that electrochemical detection is not without problems. For example, when an insufficient concentration of analyte is provided, the current flowing between working and counter electrodes of the sensor is undetectable. Because the amount of analyte detected is directly proportional to the current flowing through the sensor, small analyte concentration can result immeasurable.

Electrical sensors have also been used to determine analyte concentrations by detecting molecular binding-induced conductance or impedance changes in electrical materials (e.g., silicon, conducting polymers, and carbon nanotubes). Unfortunately, the inventors hereof have also identified many drawbacks of this technique. For instance, in addition to their large dimensions and high manufacturing costs, electrical sensors are generally highly dependent on the environment (e.g. ionic strength), less specific and less accurate.

The referenced shortcomings are not intended to be exhaustive, but rather are among many that tend to impair the effectiveness of previously known techniques as recognized by the present inventors. These problems are sufficient to demonstrate that the methodologies appearing in the art have not been satisfactory, and that a significant need exists for the techniques described and claimed in this disclosure.

SUMMARY OF THE INVENTION

In one embodiment, an integrated sensing device is capable of detecting analytes using a combination of electrochemical (EC), electrical (E), and/or optical (O) signals. In certain embodiments, the device may be an electrochemical-electrical-optical (EC-E-O) device that uses all three signals. In other embodiments, the device may be an electrochemical-optical (EC-O) device that uses electrochemical and optical signals to detect an analyte. In other embodiments, the device may be an electrochemical-optical (EC-E) device that uses electrochemical and electrical signals to detect an analyte. The device introduces synergetic new capabilities and enhances the sensitivity and selectivity for real-time detection of an analyte in complex matrices, including the presence of high concentration of interferences in liquids and in gas phases.

In some embodiments, the invention relates to electrochemical-electrical (EC-E) sensors comprising: a first electrode fabricated on a substrate; a second electrode fabricated on the substrate and spaced apart from the first electrode; a bridging material coupling the first electrode to the second electrode; an electrolyte; a counter electrode; and a reference electrode; wherein at least one of the electrodes is connected to an electronic circuit for electrochemical-electrical control and/or measurement during use.

In specific embodiments, the first electrode of the sensor is connected to an electronic circuit for applying a potential perturbation to the first electrode during use. In some embodiments the electronic circuit is a biopotentiostat.

In some embodiments, one or more of he counter electrode, reference electrode, and/or bridging material is comprised on the substrate. However, in other embodiments one or more of these components will be comprised off the substrate.

In some specific embodiments, the sensor comprise a third electrode placed apart from the first and second electrodes. In some applications, the third electrode is employed for electrochemical control and/or measurement during use. Further, in embodiments with the third electrode, the first and second electrodes may be employed for conductance measurement during use. In some cases, the electronic circuit is a tripotentiostat.

The sensors can have a surface area ratio between the second electrode and the first electrode allows an electrochemical process taking place on the second electrode and electrical properties between the first and second electrodes to be controlled and/or measured simultaneously.

The bridging material may be any suitable material as understood by a person of ordinary skill in the art, whether now existing or yet to be discovered. For example, the bridging material may be, but it is not limited to, a polymer, Si, GaAs, a metal oxide, other organic and inorganic semiconductors, a molecularly imprinted material, and/or composites made of polymers and conducting or semiconducting materials. Further, the bridging material may be provided in the form or a nanotube, a nanowire, a nanoparticle, a nanorod, and/or a nanobelt.

In one particularly specific embodiment, an electrochemical-electrical (EC-E) sensor comprises a first electrode fabricated on a substrate and coupled to a biopotentiostat circuit for applying a potential perturbation to the first electrode, a second electrode fabricated on the substrate and spaced apart from the first electrode, a bridging material fabricated on the substrate and coupling the first electrode to the second electrode, a counter electrode fabricated on the substrate and operable to close an electric circuit, and a reference electrode fabricated on the substrate and operable to control a potential of at least one of the first and second electrodes. A surface area ratio between the second electrode and the first electrode allows an electrochemical process taking place on the second electrode and electrical properties between the first and second electrodes to be measured simultaneously.

Some aspects of the invention relate to methods comprising: providing an EC-E sensor as described above or in the claims; providing an analyte; detecting a reaction product; determining a conductance and/or electrical current of the conducting or semiconducting material; determining an electrochemical signal; and detecting the analyte employing the conductance and the electrochemical signal. In some embodiments, the conductance and/or electrical current can be measured using the first electrode. Further, in some embodiments, the electrochemical signal is measured using the second electrode. Such methods may further comprise adjusting the surface area ratio between the second electrode and the first electrode to optimize performance of the EC-E sensor. In some cases the may comprise a molecule in gas phase; in others, the analyte may comprises a molecule in liquid phase.

Certain embodiments comprise a sensor including: a first electrode disposed on a substrate; a second electrode disposed on the substrate and spaced apart from the first electrode; a coupler coupling the first electrode to the second electrode; an electrolyte; a counter electrode; a reference electrode; and an optical detection system. In certain embodiments, at least one of the electrodes is connected to an electronic circuit for electrochemical-electrical control and/or measurement during use. The optical detection system can comprise a light source and an optical detector, and in certain embodiments, the light source is a light-emitting diode. The light source can be located on one side of the substrate and the optical detector located on an opposite side of the substrate from the light source in specific embodiments. In particular embodiments, the optical detector is configured to receive light transmitted from the light source and through the substrate and an analyte and its reaction products during use. In specific embodiments, the light source and the optical detector are located on the same side of the substrate.

In particular embodiments, the optical detector can be configured to receive light transmitted from the light source and reflected off of the substrate and an analyte during use. In certain embodiments, optical detector can be configured to receive light transmitted from the light source and through a wave guide during use. In specific embodiments, the optical detector can be selected from the group consisting of: a complementary metal-oxide-semiconductor (CMOS) sensor, a color sensor, a photodiode, and a charge-coupled device (CCD). In particular embodiments, a first electrode can be connected to an electronic circuit for applying a potential perturbation to the first electrode during use. In specific embodiments, the electronic circuit is a biopotentiostat. In certain embodiments, the counter electrode can be disposed on the substrate. In particular embodiments, the reference electrode can be fabricated on the substrate. The coupler may be disposed on the substrate in certain embodiments.

In certain embodiments, a third electrode can be placed apart from the first and second electrodes. In specific embodiments, the third electrode can be configured for electrochemical control and/or measurement during use. In certain embodiments, the third electrode can comprise a larger surface area than the first and second electrodes. In particular embodiments, the first and second electrodes can be configured for conductance measurement during use. In certain embodiments, the electronic circuit can be a tripotentiostat.

In particular embodiments, a surface area ratio between the second electrode and the first electrode allows an electrochemical process taking place on the second electrode and electrical properties between the first and second electrodes to be controlled and/or measured simultaneously. In particular embodiments, the coupler can comprise a polymer, Si, GaAs, a metal oxide, and other organic and inorganic semiconductors, a nanostructure, a molecularly imprinted material, and composites made of polymers and conducting or semiconducting materials. In certain embodiments, the nanostructure comprises a nanotube, a nanowire, a nanoparticle, a nanorod, and a nanobelt.

In specific embodiments, the electrolyte can be an ionic liquid. In certain embodiments, the first and second electrodes can be indium tin oxide (ITO) electrodes and the ionic liquid can be disposed over electrodes. In specific embodiments, the ionic liquid is 1-butyl-3-methylimidazolium hexafluorophosphate.

Certain embodiments may comprise an air sample delivery system. In particular embodiments, the air sample delivery system can be configured to direct air towards the substrate. Specific embodiments may comprise a wireless transmitter. In particular embodiments, the wireless transmitter can be a component in an ad hoc wireless network.

Certain embodiments include a method comprising: providing a sensor; providing an analyte; detecting a reaction product; determining a conductance and/or electrical current of the conducting or semiconducting material; determining an electrochemical signal; determining an optical property of the analyte and/or reaction product; and detecting the analyte employing the conductance, the electrochemical signal, or the optical property. In particular embodiments, the conductance and/or electrical current can be measured using the first electrode. In specific embodiments, the electrochemical signal can be measured using the second electrode. Certain embodiments can comprise adjusting a surface area ratio between the second electrode and the first electrode to optimize performance of the EC-E sensor. In particular embodiments, the analyte can comprise a molecule in gas phase or a liquid phase.

Certain embodiments include a sensor comprising: an electrolyte; a first electrode coupled to the electrolyte; a second electrode coupled to the electrolyte; a device configured to apply a voltage between the first and second electrodes, wherein during use the voltage induces an electrochemical reaction on the first electrode and the electrochemical reaction on the first electrode causes a change in an optical property of the electrolyte; and an optical system configured to measure the change in the optical property of the electrolyte.

Particular embodiments include a method comprising: providing a sensor; providing an analyte; detecting a reaction product; determining an electrochemical signal; determining an optical property of the analyte or reaction product; and detecting the analyte employing the optical property and the electrochemical signal. In certain embodiments, the electrolyte is configured to receive an analyte in a gas phase or a liquid phase.

In particular embodiments, the analyte can be selected from the group consisting of: nitroaromatics such as trinitrotoluene (TNT), dinitrotoluene (DNT), picric acid (PA); nitramines such as cyclotrimethylenetrinitramine (RDX), octogen (HMX), Trinitrophenyl-n-methylnitramine (tetryl), nitroesters such as nitroglycerine (NG), ethylene glycol dinitrate (EGDN), Pentaerythritol tetranitrate (PETN); nitrocompounds such as nitromethane; nitrates such as urea nitrate, and tagging agents such as dimethyldinitrotoluene, nitrobenzene, nitrotoluene and their derivatives. In certain embodiments, the electrolyte can be supported on a substrate. In specific embodiments, the substrate can be a transparent or semitransparent material. In specific embodiments, the substrate can be flat and reflective.

In certain embodiments, the substrate can be ITO (Indium-Tin-Oxide), and the substrate can be configured to serve as the first electrode and as an optical window in the optical system.

In particular embodiments, the electrolyte can contain one or more additives to enhance the penetration or solubility or chemical reaction of an analyte into the electrolyte and/or the electrochemical reaction. In specific embodiments, the electrolyte is an ionic liquid such as imidazolium derivative or an organic solvent with salts. In particular embodiments, the imidazolium derivative can be 1-butyl-3-methylimidazolium hexafluorophosphate. Certain embodiments can comprise a third electrode configured to control the voltage between the first and second electrodes. In particular embodiments, the first, second and third electrodes can be coupled to a potentiostat for controlling and detecting the electrochemical reaction. In certain embodiments, the first, second and third electrodes can be either inserted in the electrolyte or disposed on the substrate. In particular embodiments, the first electrode can be a thin ITO (Indium-Tin-Oxide) film coated on a transparent substrate. In certain embodiments, the first electrode can be a thin metal or carbon film deposited on the substrate. In particular embodiments, the first electrode can comprise interconnected conductive lines deposited on the substrate. In specific embodiments, the optical system can comprise an optical detector and a light source. In particular embodiments, the light source can be ambient light, a light emitting diode or a laser diode. In particular embodiments, the optical system can comprise an imaging or video system. In specific embodiments, the imaging or video system can comprise a webcam, digital camera or a charge-coupled device (CCD).

The term "coupled" is defined as connected, although not necessarily directly, and not necessarily mechanically.

The terms "a" and "an" are defined as one or more unless this disclosure explicitly requires otherwise.

The term "substantially," "about," and their variations are defined as being largely but not necessarily wholly what is specified as understood by one of ordinary skill in the art, and in one non-limiting embodiment, the substantially refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 2A-2C show a bare sensor, a sensor after a metal deposition, and a sensor after a polymer deposition, in accordance with embodiments of the present disclosure.

DESCRIPTION OF ILLUSTRATIVE EMBODIMENTS

The invention and the various features and advantageous details are explained more fully with reference to the non-limiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only and not by way of limitation. Various substitutions, modifications, additions, and/or rearrangements within the spirit and/or scope of the underlying inventive concept will become apparent to those skilled in the art from this disclosure.

Electrochemical-Electrical Embodiments

Certain embodiments of the present disclosure comprise systems and methods for integrated electrochemical and electrical detection. In one embodiment, the present invention integrates electrochemical and electrical (EC-E) sensing elements into a single device operable to simultaneously perform electrochemical and electrical detection, thus providing new capabilities compared to the single detection mode typically provided by existing sensors. The EC-E sensors disclosed herein provide unique selectivity features for real-time analyte detection in liquids, gases, cultures, tissues, and the like.

In one embodiment, an EC-E sensor may be able to detect an analyte either via electrochemical current changes ($\Delta I_{ec}$) of a conducting or semiconducting material, conductance changes of the conducting or semiconducting material ($\Delta G$), or a combination of both. The combination of both parameters ($\Delta I_{ec}$, $\Delta G$) is particularly advantageous because it enhances selectivity for detection of analytes in complex matrices, even in the presence of interferents with much higher concentrations than the concentration of the analyte. In some embodiments, a nanoscale version of the EC-E sensor may allow for the detection of very low concentrations of analytes.

Figure 1:
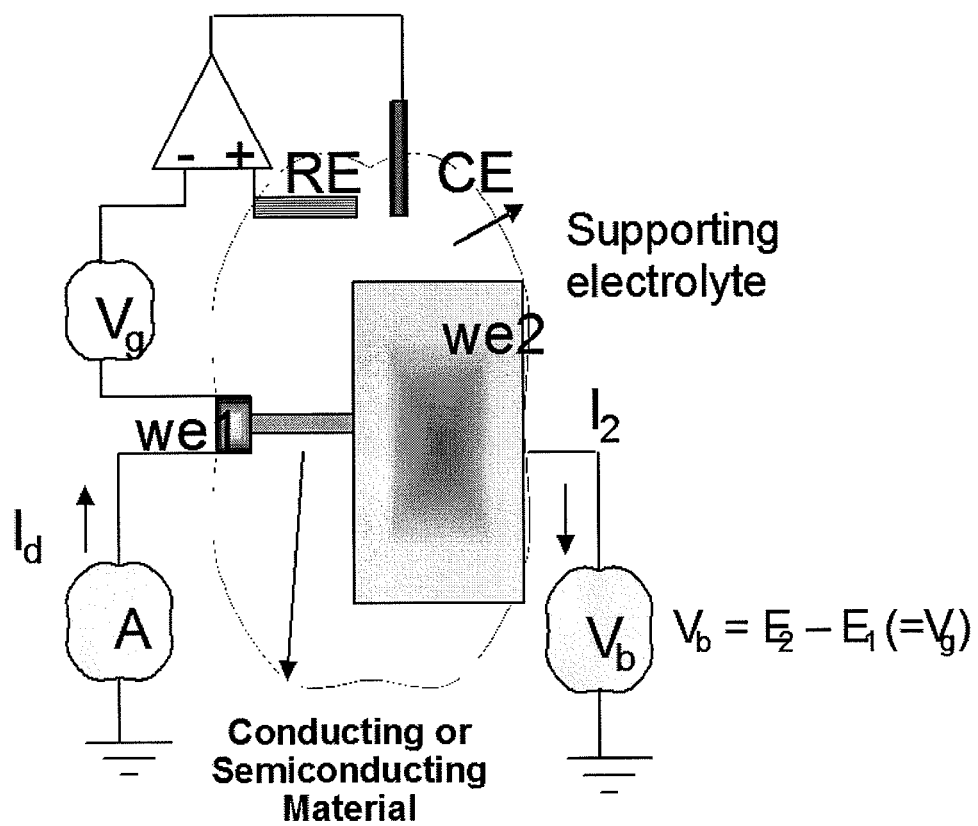
FIGS. 1 and 1A show diagrams of an EC-E sensor in accordance with embodiments of the present disclosure.

FIG. 1 shows a diagram of an EC-E sensor in accordance with embodiments of the present invention. The EC-E sensor may include a pair of asymmetric working electrodes WE1 and WE2 fabricated on a silicon chip or other suitable substrate. In one embodiment, electrodes WE1 and WE2 may have different surface areas, and may be separated by a gap varying from, for example, microns to nanometers. For example, WE2 may have a larger area compared to WE1. The surface area ratio (WE2/WE1) is advantageous when it becomes necessary to decrease a contribution of electrochemical and capacitive currents from WE1 ($I_{1,ec}$) on the drain current ($I_1$) taken from WE1, where $I_1$ may be approximately equal to $I_d$, which may be directly proportional to the conductance (G). Further, the surface area ratio (WE2/WE1) may increase an electrochemical product concentration produced on WE2, and thus it may improve the sensitivity to electrochemical current obtained from WE2 ($I_{2,ec}$). In operation, WE1 and WE2 may represent source and drain (working) electrodes. A bias potential ($V_b$) may be applied between WE2 and WE1.

The EC-E sensor may also include a counter electrode (CE) to close the electrical circuit responsible for the electrochemical currents. The amplifier (A) of FIG. 1 represents part of the bipotentiostat circuit used to apply potential perturbation on WE1, which is measured against a reference electrode (RE).

Referring again to FIG. 1, a conducting or semiconducting material may bridge the two electrodes. Examples of conducting material include conducting polymers, metal oxides, nanostructures (e.g., nanotubes, nanowires, nanoparticles, nanorods, nanobelts, nanoparticles, or molecularly imprinted materials). Alternatively or in addition to the above, conducting materials may include composites made of polymers and conducting or semiconducting materials. The conducting material may allow for the detection of electrical current through the material between the two electrodes WE1. and WE2 under a bias voltage ($V_b$).

The sensibility of conductance changes on the conducting or semiconducting material may be increased with a higher surface to volume ratio. This situation is reached when small but continuous and stable amounts of conducting material are immobilized or deposited into the gap. For example, use of few polymer strands, nanowires and nanotubes allows detection of conductance changes from concentrations of analytes as low a pM.

Conductivity measurements of the conducting or semiconducting material may also be performed through a drain current ($I_d$) from first electrode (WE1). An electrolyte may be provided to the device may give electrolytic conductance to the device. The supporting electrolyte may be liquid, polymer, semi-liquid or solid and may be composed of ionic liquids or solid or of gels or aqueous or organic ionic solutions. The supporting electrolyte may be held by a cell in intimate contact with the device surface. The second electrode (WE2) may be used to determine the electrochemical reduction/oxidation of analytes or analyte derivatives. An electrochemical potential (E1=$V_g$), may be applied between the drain electrode (WE1) and a reference electrode (RE) coupled to a supporting electrolyte. Moreover, $V_g$ may be gated through the supporting electrolyte from the reference electrode (RE) and electrochemical measurements may be monitored from a differential current between the electrodes determined by:

$$I_{2,ec} = I_2 - I_d \qquad 1$$

where $I_2$ is this the current from WE2 as pictured in FIG. 1.

The sensitivity of the EC-E sensor may be adjusted and the selectivity may be further improved by optimizing, for example, the geometry and dimension of the electrodes, the length of the gap, amount and geometry of conducting material bridging the gap, chemical modification, as well as gate and bias potential control. For example, the geometry and dimension of the WE1 and WE2 electrodes, and in particular, the area ratio (WE2/WE1), may be altered and improved through an electrochemical selective deposition of metal on the second electrode (WE2). Several metals such as gold, platinum, palladium, mercury, nickel, silver, copper, cadmium, zinc, etc. may be suitable. By adjusting the geometry and dimension of WE1. and WE2, the electrodes' roughness and area may increase and allow for a reduction of the gap size from few micrometers to a few hundreds or a few nanometers.

Figure 1A:
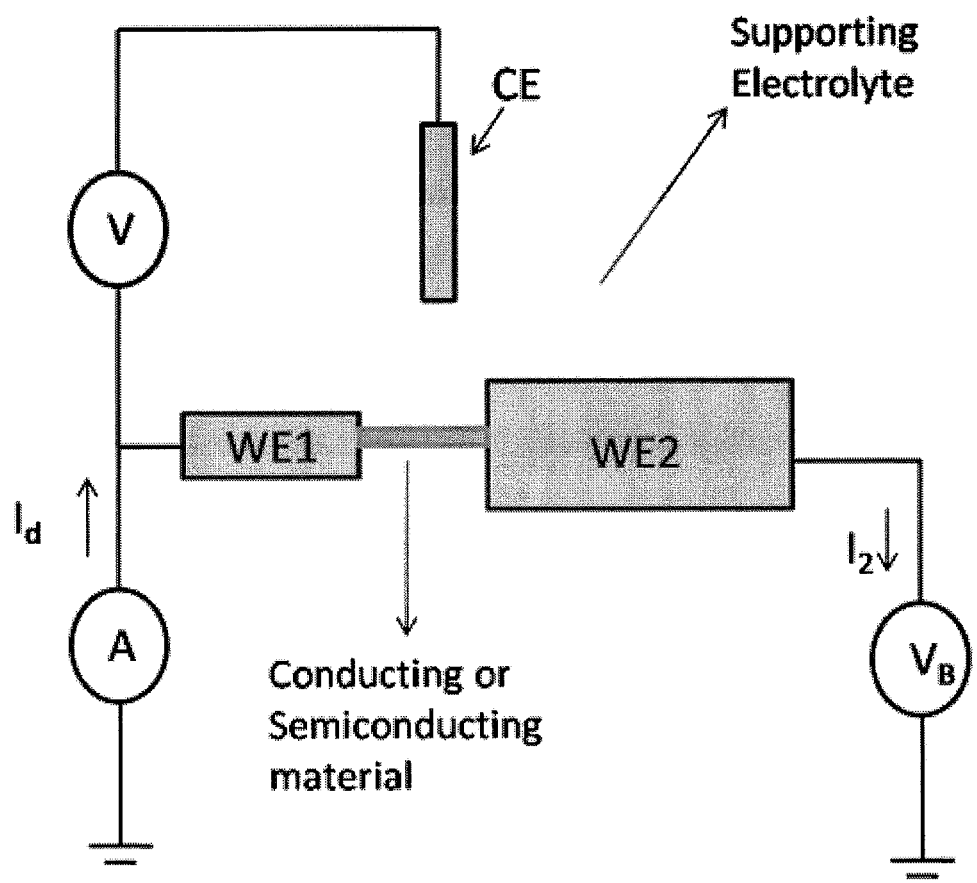

Referring now to FIG. 1A, the illustrated embodiment shows a schematic diagram of an electrical and electrochemical sensor. This embodiment uses only a current sink or counter electrode (CE) and two working electrodes (WE1 and WE2) as described in FIG. 1.

FIGS. 2A and 2B show optical back and dark field images of a device before and after a metal electrodeposition of gold to enlarge the surface area of WE2, respectively. FIG. 2C shows the device of FIG. 2A after a polymer deposition. The higher brightness shown in FIG. 2B indicates increasing roughness of the WE2. It should be noted that the gap between WE1 and WE2 decreases in size as the surface area of WE2 increases. In some embodiments, smaller gaps between WE1 and WE2 may provide better sensitivity for electrical detection although the exact dimensions may depend upon the particular application.

The EC-E selectivity enhancement may vary based on the properties of the conducting material across the two electrodes WE1 and WE2. Alternatively, modification of the conducting material, electrode surface, chip surface, substrate surface, or the use of a supporting electrolyte with redox mediator molecules or other organic or biological recognizing elements, such as, but not limited to, cyclodextrins, crown ethers, peptides, proteins, enzymes, antibodies, aptamers, nucleic acids and peptide nucleic acids able to interact chemically or stereo-selectively with the analyte may be used to enhance the selectivity of the EC-E sensor. In one respect, the supporting electrolyte may be liquid or semi-solid or solid and chemically modified to avoid interferents.

In one embodiment, the present invention provides for the integration of many EC-E sensors on single chip or substrate. For a single analyte detection, even when materials and modification of the chip is uniform all over its multiple parallel devices, gated and biased potential control on different devices allows obtaining a combination of pair of conductance and electrochemical signals ($\Delta I_{ec}$, $\Delta G$) that ensures discrimination of analyte of interest in complex matrices.

FIGS. 3A-3G show diagrams of several reaction pathways that may be accounted and applied to EC-E detection in liquid or gas phases according to certain embodiments of the present invention. The following outlines the type of detection, the analyte, and the effect on the conducting or semiconducting material.

CASE A: Independent Electrical-Electrochemical (E-EC) Detection

Figure 3:
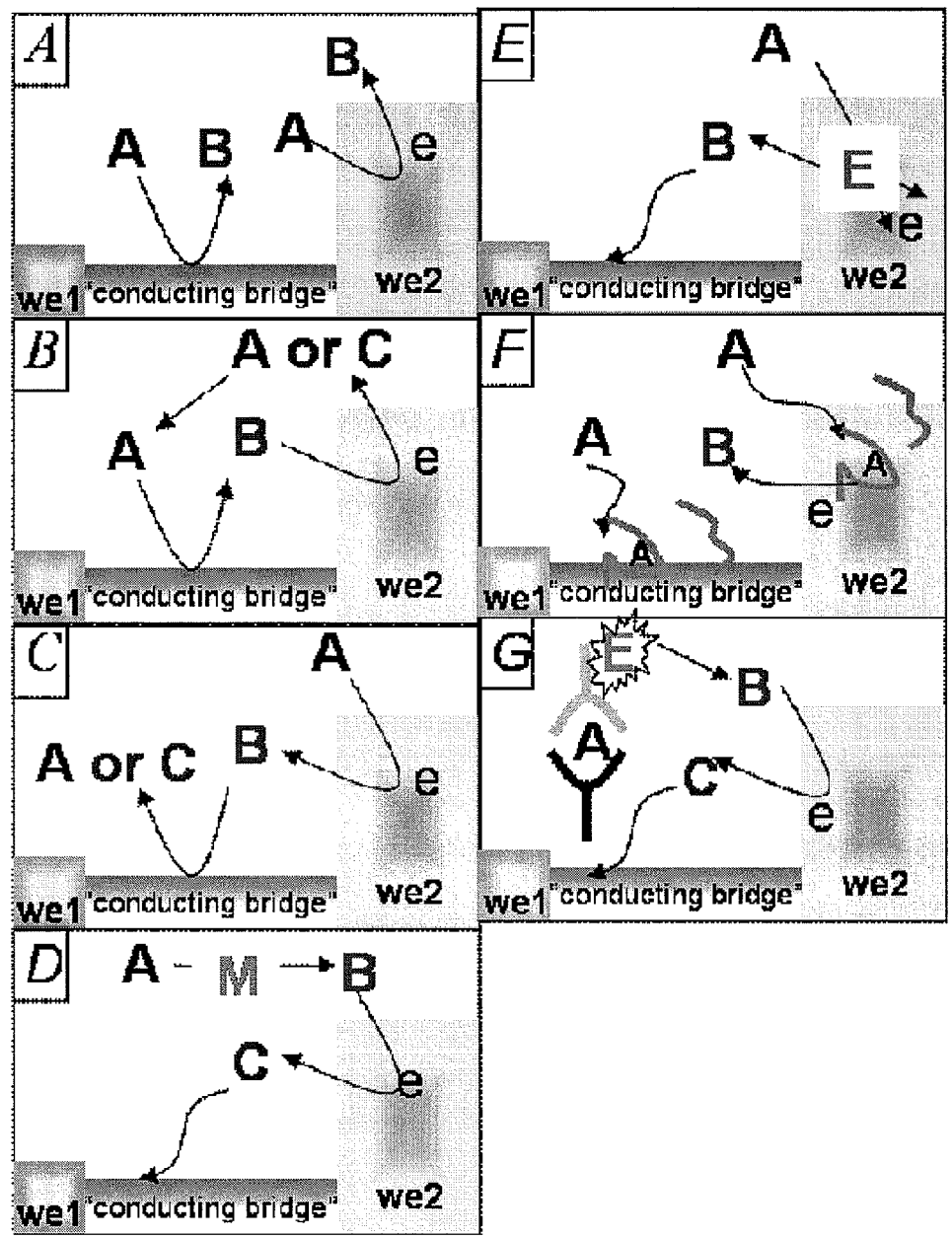
FIGS. 3A-3G show diagrams of EC-E sensors used in different applications, in accordance with embodiments of the present disclosure.

Referring to FIG. 3A, when analyte A is electrochemically active and irreversible arrives to the device surface, the analyte may modify the conductance of the conducting or semiconducting material ("conducting or semiconducting bridge") and may be electrochemically irreversible reduced or oxidized on WE2, providing independent drain current ($I_d$) and electrochemical current ($I_{2,ec}$) changes. One example is the detection of ascorbic acid.

CASE B: Dependent Electrical-Electrochemical (E-EC) Detection

Referring to FIG. 3B, analyte A may be chemically converted to B in the conducting or semiconducting material and may electrochemically oxidize or reduce to another product C or revert back to B (if it is electrochemical reversible species). Chemical conversion of A to B may be induced by chemical modification of the conducting or semiconducting bridge or when conducting or semiconducting bridge native material is sensitive to redox changes from A.

CASE C: Dependent Pure Electrical-Electrochemical (E-EC) Detection

Referring to FIG. 3C, analyte A may be oxidized or reduced electrochemically (EC detection) and the electrochemical product B may be detected on the conducting material (E detection). For example this reaction pathway may be used to detect nitro-explosives that produce intermediate reduction products that can oxidize or reduce the conducting or semiconducting material bridge. Additionally or alternatively, the detection of electroactive compounds of analyte A which may include reversible or quasi-reversible redox features in presence of interferences that are also electrochemically active (A') but irreversibly oxidized or reduced. Under this condition, only the electrochemical active product (B) coming from analyte of interest (A) may be electrically detected. For example, low dopamine concentrations (ranging from about a hundreds nM—to about a few micromolar range) can be detected in presence of high concentrations (mM range) of ascorbic acid, uric acid or other similar interferents. This detection scheme is referred to as an electrochemical-assisted electrical detection.

CASED: Chemical Mediated Electrochemical Electrical (EC-E) Detection

Referring to FIG. 3D, analyte A may be chemically transformed with assistance of mediator M, and then EC and E detected as described in FIGS. 3A-C described above. The chemical mediator may be dissolved in the supporting electrolyte (SE) or immobilized on the electrodes or chip surface. In one respect, analyte A may be acetone and may be detected using hydroxylamine as a mediator to produce an electrochemically active oxime derivative.

CASE E: Redox Catalyst Mediated Electrochemical Electrical (EC-E) Detection

Referring to FIG. 3E, analyte A may be a catalyst target. An inorganic or biological catalyst may be chemically wired to the larger electrode (e.g., WE2) which may pump electrons for the regeneration of the catalyst. The catalyst product reaction product may be detected on the conducting or semiconducting material, where the sensitivity for detection may be increased due to the catalytic effect. It is noted that a combination of catalysts may widen this application. For example, detection of aldehydes and alcohols may be made using quino-dehydrogenases immobilized on WE2. These enzymes produce acid products that can increase the conductance of pH sensitive conducting material.

CASE F: Recognizing Element Mediated Electrochemical Electrical (EC-E) Detection Referring to FIG. 3F, electrodes and conducting material may be modified with an organic molecule, biomimic, or biological recognizing element which may selectively trap an analyte that may be electrochemically active. The active recognizing layer on WE2 serves as a preconcentrator of the analyte, which may be electrochemically oxidized or reduced. The recognition of the analyte on the conducting or semiconducting material may induce conformational, charge, or pH changes that may be transduced as a change in conductance. This particular case can be applied to, for example, the detection of heavy metal ions using peptides as probes.

CASE G: Label-Dependent Electrochemical Electrical (EC-E) Detection

Referring to FIG. 3G, commercially available enzyme-labeled for detection of many hormones and tumor markers used in immunological assays combined with the application of EC-E detection may improve detection performance and to simplify instrumentation. Probes labeled with commonly used enzymes such as peroxidase and alkaline phosphate may be used to detect enzymatic products from antibodies immobilized on the EC-E devices which may have include a incubation of the sample. After rinsing and addition of enzyme reactants, the presence of enzyme may be developed by electrochemical detection of enzymatic products and conductance change due to oxidation of the conducting or semiconducting material. In cases where an unlabeled probe is immobilized on the conducting material, and in particular in the area bridging WE1 and WE2, the conductance changes may be detected directly during sample incubation. Later EC-E detection may subsequently be performed.

In one embodiment, a number of EC-E sensors may be applied to a multiple analyte detection in liquid and gas phases. Because integration of many devices may be achieved in on single chip, simultaneous monitoring of multiple analytes may be achieved by adjusting the chemical modification as well as gated and biased potentials. Detection of analytes in liquid phase involved delivery of the sample through injections to bath cell or through a microfluidic system, while detection of chemical vapors comprise diffusion gases through a supporting electrolyte layer.

The following example is included to demonstrate specific embodiments of this disclosure. It should be appreciated by those of skill in the art that the techniques disclosed in the example that follows represent techniques discovered by the inventors to function in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the scope of the invention.

Figure 4:
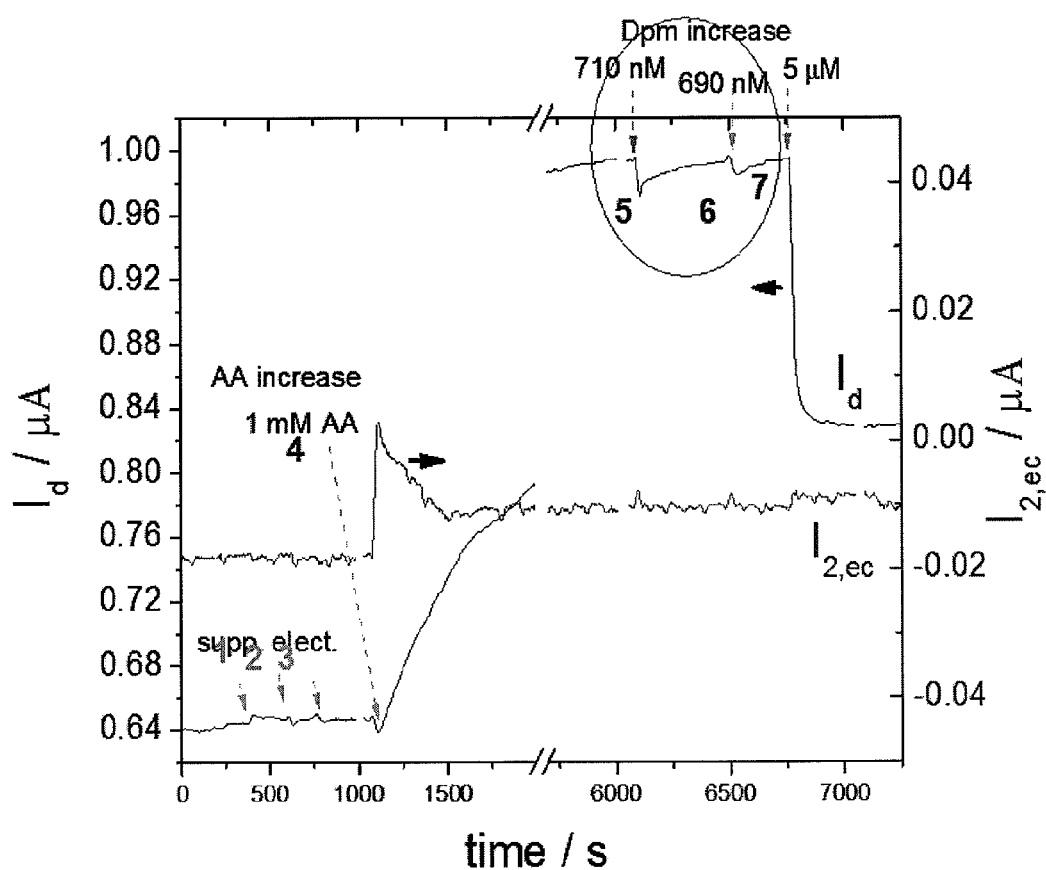
FIG. 4 shows a graph of an output of the EC-E sensor in accordance with embodiments of the present disclosure.

An illustrative, non-limiting experiment demonstrating the capability of EC-E nanosensor to detect the neurotransmitter dopamine (Dpm) in presence of its major physiological, ascorbic acid (AA), at a concentration level three orders of magnitude higher is shown. Referring to FIG. 4, the time course of EC-E sensor made of conducting bridge of polyaniline (e.g., as shown in FIG. 2C) is shown. Electrochemical current ($I_{2,ec}$) and drain ($I_d$) current are monitored simultaneously towards the injection of a supporting electrolyte (50 mM $H_2SO_4$), AA (1 mM), and Dpm (710 nM, 610 nM and 5 µM, respectively). It is noted that the voltages used in this examples are as follows: $V_g$=E1=200 mV vs Ag/AgCl and E2 =450 mV vs Ag/AgCl.

Drain current ($I_d$) and electrochemical current from WE2 ($I_{ec,2}$) are simultaneously recorded during successive injections of the neurotransmitter "dopamine" (Dpm) (nanomolar (nM) or micromolar (uM) range) in the presence of three orders of magnitude higher concentration of ascorbic acid (AA). The experiments resembles physiological AA/Dpm concentration ratio. Initial injections of supporting electrolyte are performed to monitor stability of conducting bridge towards injections. No significant changes are observed due to injection and mechanical stirring itself. After that, AA concentration was injected to reach milimolar (mM) range. An increase of $I_d$ is observed in parallel with an increase of $I_{2,ec}$. The increase of $I_{2,ec}$ may be due to irreversible oxidation of AA to dehydroascorbic. The cause of $I_d$ changes may be due to the reduction of the polymer. Given the current experimental conditions, reduction of the conductor material is transduced into an increase of conductance (observed as important increase in $I_d$ over the time). This is an example of Case A previously described in the application cases.

Next, injections of Dpm performed after AA do not produce significant changes of electrochemical component current ($I_{2,ec}$) since electrochemical detection may not be sensitive to oxidation of hundred of nanomolar (nM) or micromolar (uM) range of Dpm. However, the electrochemical products of Dpm (dopaminoquinones, DQ) have an important effect on the conducting material, and thus $I_d$. DQ molecules are able to oxidized the conducting polymer material, and counteracts the reducing effect of AA, the major component in the media. Detection on a micromolar concentration change of Dpm are clearly observed by a sharp decrease of $I_d$, while detection of hundred of nanomolar concentration changes of Dpm may be less evident and may require better stabilization of baseline conditions to be addressed. This is an example of EC-assisted E detection described above.

Concentrations of a neurotransmitter three order of magnitude smaller than its major physiological interferent (AA) can be easily and continuously detected with the sensor of the present disclosure.

Electrochemical-Electrical -Optical Embodiments

Figure 5:
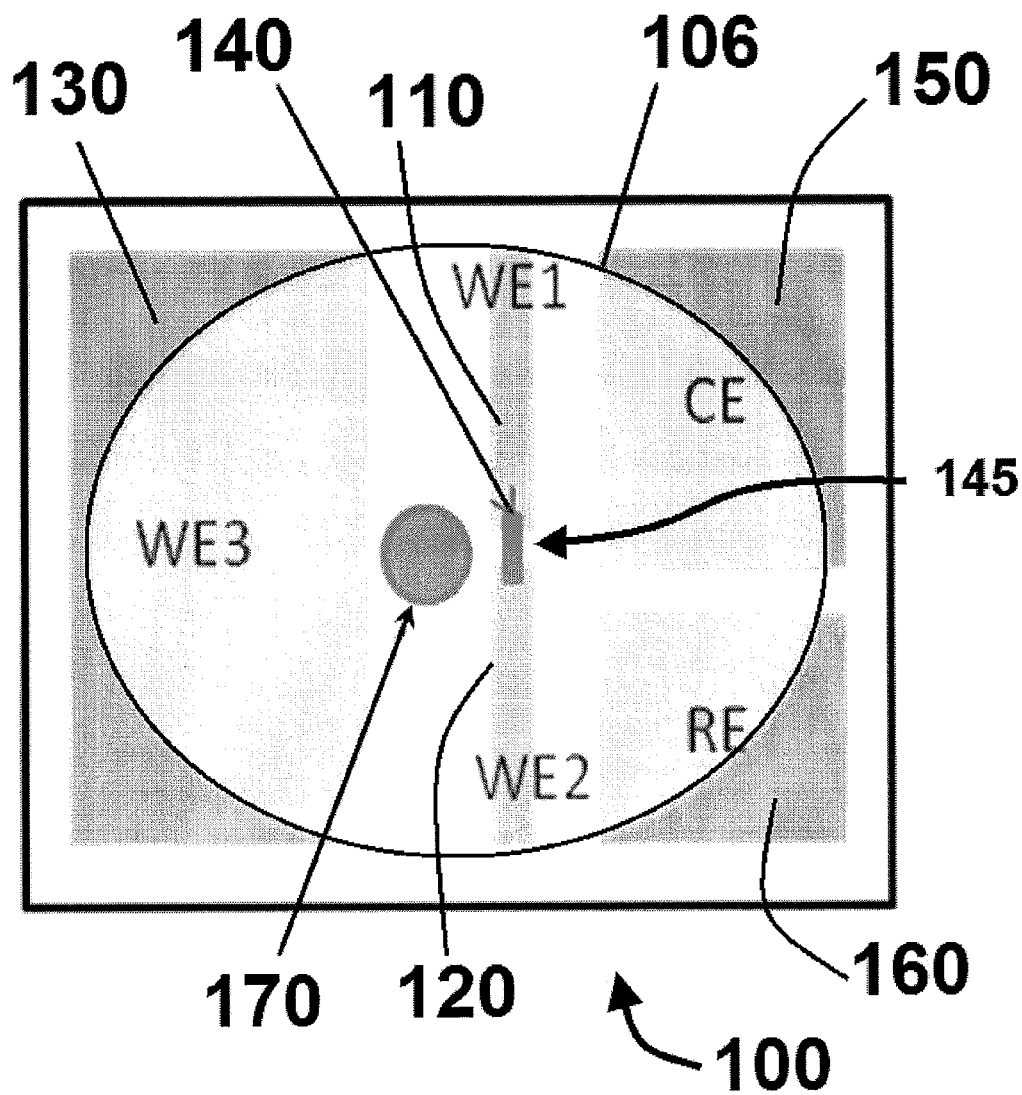
FIG. 5 shows a schematic diagram of a top view of an EC-E-O sensor in accordance with embodiments of the present disclosure.
Figure 6:
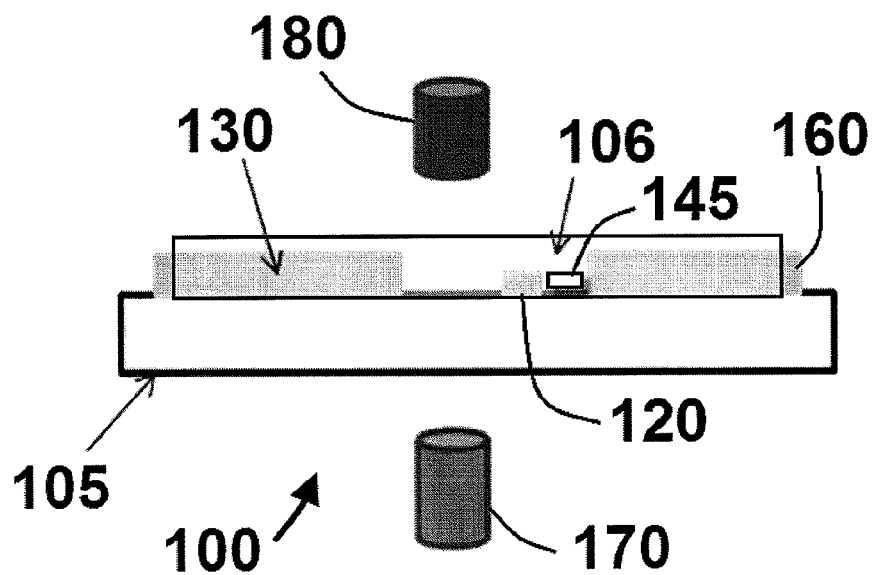
FIG. 6 shows a schematic diagram of a side view of an EC-E-O sensor in accordance with embodiments of the present disclosure.

Referring now to FIGS. 5 and 6, an exemplary embodiment of an EC-E-O sensor 100 comprises a first working electrode 110 coupled to a second working electrode 120 via a coupling 140 comprising a conductive or semiconductive material. In the embodiment shown, sensor 100 further comprises a third working electrode 130, a counter electrode 150, and a reference electrode 160. In this embodiment, sensor 100 also comprises an optical detection system comprising an optical sensor 170 and a light source 180.

Sensor 100 can be operated in several different ways: (1) detection of electrochemical current changes ($\Delta I_{ec}$); (2) detection of electrical conductance changes of a conducting material ($\Delta G$); (3) detection of optical absorption signal ($\Delta A$); or (4) a combination of any two or all three of the detection modes. The combination of multiple detection parameters ($\Delta I_{ec}$, $\Delta G$, $\Delta A$) gives arise to an orthogonality that enhances the selectivity for detection of analytes in complex matrices, especially in the presence of interferents with much higher concentrations than the analytes themselves. It also improves the reliability due to redundancy introduced by detecting the three signals.

In the embodiment shown, the electrodes are supported on a solid state substrate 105 and covered with an electrolyte 106. In this embodiment, first and second working electrodes 110 and 120, along with coupling 140 are used to form a junction 145 and measure the conductance of the junction. In the embodiment shown, junction 145 is a conducting polymer junction. Third working electrode 130 can be used for electrochemical detection. The potentials of working electrodes 110, 120 and 130 can be controlled with respect to reference electrode 160. In certain embodiments, with the help of counter electrode 150 and a potentiostat (not shown), currents from third working electrode 130 (and possibly first and second working electrodes 110 and 120) can be detected. In other embodiments, the electrochemical detection is accomplished by controlling the currents of working electrodes 110, 120 and 130, and detecting the potentials of the three working electrodes with a galvanostat (not shown).

The optical detection can achieved with light source 180 and optical sensor 170 (e.g., a photodetector), which is achieved in several ways described below. In exemplary embodiments, optical sensor 170 may be used as an imaging device, a video device or simply to detect changes in light intensities or colors.

In certain embodiments, third working electrode 130 comprises a large surface area so that electrochemical reactions take place on third working electrode 130 quickly and generate a large amount of reaction products that can be detected using the polymer junctions via conductance change and the optical detection means via optical absorption. The use of the large surface area for third working electrode 130 also results in relatively large electrochemical current that can be more easily detected.

In certain embodiments, third working electrode 130 detects analytes via electrochemical current at various potentials, and also generates reaction products. In certain embodiments, first and second working electrodes 110 and 120 have relatively small surface areas, which are preferably coated with insulation layers to minimize electrochemical reactions. Coupling 140, which comprises a conductive or semiconductive material (for example, a conductive polymer), is deposited or placed between first and second working electrodes 110 and 120 to form a conduction pathway between first and second working electrodes 110 and 120. The conductive material can be used in an electrochemical transistor configuration where first and second working electrodes 110 and 120 are the source and the drain electrodes and the gate potential (Vg) is applied via reference electrode 160, together with counter electrode 150 and a potentiostat (not shown). The source-drain current (Isd) is monitored with a bias voltage (Vbias) between first and second working electrodes 110 and 120 at various gate potentials, Vg.

When the analytes or reaction products of the analytes reach junction 145, it induces a change in the conductance of junction 145 via either specific interactions, shift of redox potential of the conducting polymer materials or other mechanisms caused by the analytes or the reaction products. In certain embodiments, it is also preferred to place first and second working electrodes 110 and 120 close to third working electrode 130 so that the reaction products can quickly reach junction 145.

Although sensor 100 can be used with different kinds of electrolytes, ionic liquid is preferred in certain embodiments due to: (1) the large potential window that can be operated without causing unwanted electrochemical reactions; and (2) the low vapor pressure, allowing a thin layer of the ionic liquid to be used for an extended period of time without evaporation. Other advantages of room temperature ionic liquids include selectivity towards analytes and dissolution of electrochemical, conductimetric and optical detection mediators.

In certain embodiments, the thin layer is desirable for rapid diffusion of analytes from air to the sensing elements on the solid substrate, which is particularly useful for detecting analytes in air. Room temperature ionic liquids with acidic properties can offer an additional advantage in terms of detectable products variety. Examples of this group include the imidazolium derivative ionic liquids.

Figure 7:
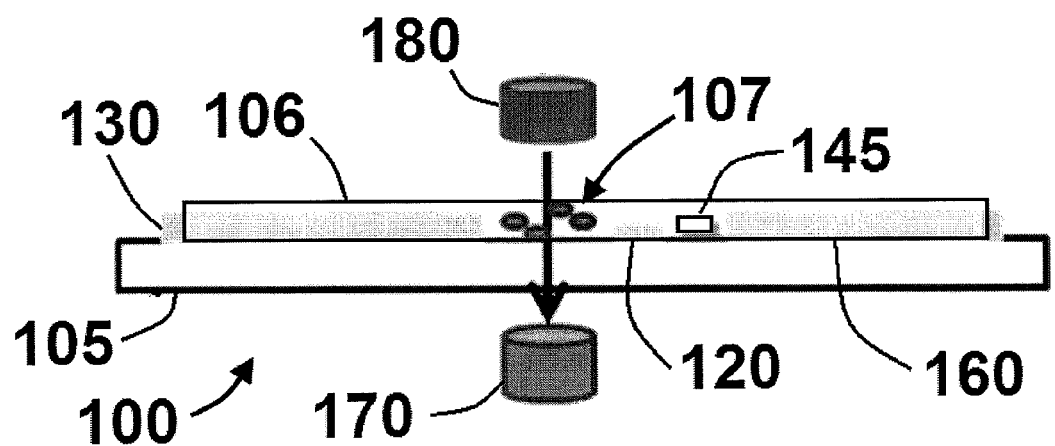
FIG. 7 shows a schematic diagram of a side view of an EC-E-O sensor with a first configuration for the optical sensor in accordance with embodiments of the present disclosure.
Figure 8:
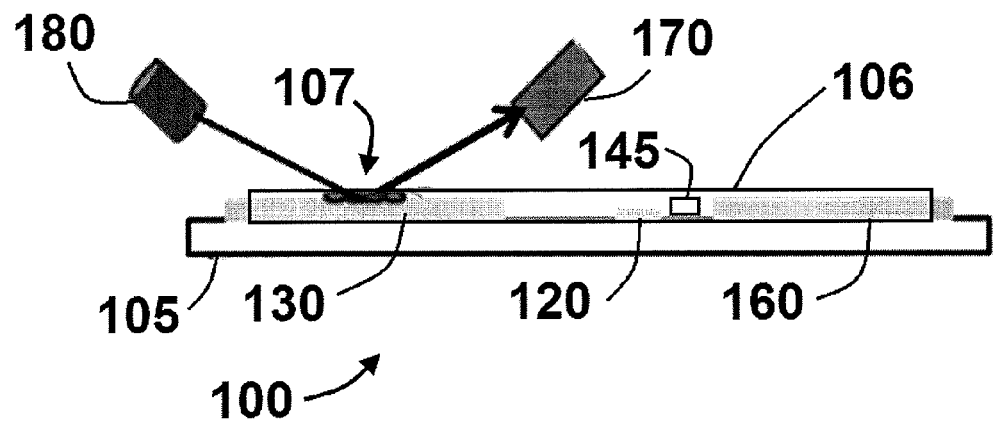
FIG. 8 shows a schematic diagram of a side view of an EC-E-O sensor with a second configuration for the optical sensor in accordance with embodiments of the present disclosure.
Figure 9:
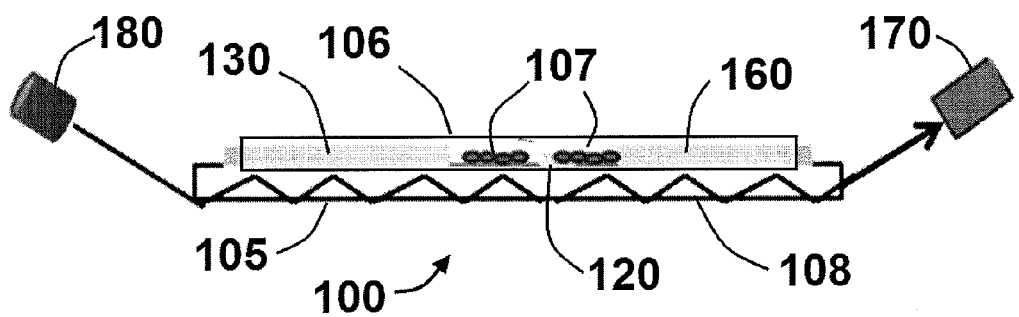
FIG. 9 shows a schematic diagram of a side view of an EC-E-O sensor with a third configuration for the optical sensor in accordance with embodiments of the present disclosure.

Referring now to FIGS. 7-9, schematic views are shown of various embodiments of a sensor employing different optical sensor configurations. In certain embodiments, the preferred implementation of optical detection is to detect the optical absorption of the analytes or/and reaction products on the solid state substrate at a specific wavelength or as a function of wavelength to produce an optical spectrum with features associated with the concentrations and identities of the analytes and their reaction products.

As shown in FIG. 7, in certain embodiments substrate 105 comprises a material through which light can be transferred (e.g., a transparent or translucent material). In such embodiments, light source 180 can be placed on one side of substrate 105, and optical sensor 170 can be placed on the opposite side of substrate 105. Light from light source 180 can also be transmitted through an analyte 107, such that analyte 107 affects the properties (e.g. the wavelength, intensity, etc.) of the light received by optical sensor 170.

Depending on the properties of analyte 107, the right wavelength source can be used as well as an optical sensor 170 (e.g. a photodetector) for a selected range where the desired analyte 107 absorbs or transmits light. A broad range of frequencies can also be monitored by using a light source with a broad spectrum and either a broad spectrum optical sensor or more than one sensor with the desired wavelength sensitivity. Light in the ultra violet, visible and infra red spectra can be used as source of optical excitation increasing the selectivity by selecting a wavelength where only the desired analyte will absorb or transmit light compared to common interferents.

As shown in FIG. 8, in certain embodiments, light from light source 180 (e.g., a light emitting diode (LED)) can be reflected from analyte 107 and the solid state substrate 105 (or the working electrodes), and detected with optical sensor 170. Analyte 107 will affect the properties of the light reflected to optical sensor 170 and the composition of analyte 107 may be determined based on the properties of the light received by optical sensor 170. In this embodiment, the incident light can be reflected on the working electrode (WE) where the electrochemical reactions will occur, to be detected with a photodetector.

As shown in FIG. 9, in certain embodiments a waveguide 108 can be created on the surface of 105 substrate, which can increase the effective optical path allowing for the detection of a smaller concentration of analyte 107. A material can be coated on top of substrate 105 that can produce internal reflection of the incident light, or substrate 105 itself can be used as a waveguide. When analyte 107 is close to the surface it will interact with the light being reflected several times through waveguide 108, increasing the effective path length of the light.

If an analyte can fluoresce, light with the specific wavelength to excite the analyte can be chosen and a detector or optical sensor with the wavelength of the fluorescent light can be used.

The sensitivity, response time and detection range of sensor 100 can be adjusted and improved by optimizing geometry and dimension of electrodes and gap, nature, amount and geometry of coupling 140 (e.g., the conducting material bridge), chemical modification as well as gate and bias potential control and by enhancing the path length of the optical signal via the use of waveguides.

Geometry and Dimension of Electrodes

In certain embodiments, working electrode 130 has a large area in order to maximize the area exposed to the analytes, which will increase of the amount of material reduced to be detected. Working electrodes 110 and 120, where coupling 140 is deposited should be in between working electrode 130 and counter electrode 150 in order to enhance the transport of the reduced analyte 107 towards junction 145. The geometry of both counter electrode 150 and working electrode 130 can be sharper at the end to create a higher electric field between them to increase the transport of analyte 107 to coupling 140.

Geometry and Dimension of the Gap

In certain embodiments, a smaller gap between first working electrode 110 and second working electrode 120 (e.g., the distance between first working electrode 110 and second working electrode 120) provides improved sensitivity for electrical detection. However, in this case collection of electrochemical species generated in the working electrode 130 is needed in the bridge and the size of the gap can be shrunk up to a limit that does not preclude diffusion of those electrochemically generated species. Because of this, preferred gap sizes have been defined between hundreds of nanometers and tens of nanometer. The width can also be optimized, smaller to improve sensitivity or longer to increase the dynamic range of the sensor by having more material and a wider area of conductive material where the analyte can interact Nature of Conducting Bridge Coupling 140 (e.g. the "conducting bridge") may comprise conducting polymers, metal oxides, nanostructures (nanotubes, nanowires, nanoparticles, nanorods, nanobelts), nanoparticles and their assemblies, molecularly imprinted materials as well as composites made of polymers and conducting or semiconducting materials can be used as conducting materials bridging the gap.

Chemical Modification

In certain embodiments, extra selectivity enhancement can be achieved by carefully selecting material used to form coupling 140 bridged across the first and second working electrodes 110 and 120. Extra selectivity enhancement may also be achieved by modification of the bridging material itself, electrode surface, chip surface or supporting electrolyte using redox mediator molecules or other organic or biological recognizing elements, like cyclodextranes, crown ethers, peptides, proteins, enzymes, antibodies, aptamers, nucleic acids and peptide nucleic acids able to interact chemically or stereo-selectively with the analyte as well as chemical functional groups like amides, carboxylic acids, sulfurs, that can be introduced onto the conductive material for strong and specific interaction with the analyte. The supporting electrolyte 190 can be liquid or semi-solid or solid and chemically modified to avoid interferents.

Potential Control

In certain embodiments, integration of multiple sensors can be achieved on single chip. For a single analyte detection (even if materials and modification of the chip are uniform all over its multiple parallel sensors), gated and biased potential control on different sensors allows obtaining a combination of a pair signals. The first signal is a conductance signal in the junction and the second signal is an electrochemical signal from the junction and the third working electrode ($\Delta I_{ec}$, $\Delta G$) that ensures discrimination of analyte of interest in complex matrixes. Multiple potential control can be used to control the potential of all the working electrodes with respect to the reference electrode for cases where the potentials needed for analyte reduction are different from those applied to the conductive material junction.

Operation Modes

Sensor 100 can be operated in multiple different modes, which can detect several reaction pathways. Some of the operations modes have been briefly described earlier. Additional examples include Mode 1: Fixed Potential In this mode, a fixed bias voltage is applied across first working electrode 110 and second working electrode 120, and the current across the two electrodes is monitored. In the meantime, a fixed potential is applied to working electrode 130, on which electrochemical reaction of one or more analytes 107 take place and reaction products of the analytes are generated. Detection of analyte(s) 107 is achieved by detecting both the electrochemical current at working electrode 130 due to the analytes, and conductance of the junction 145 (between first working electrode 110 and second working electrode 120) due to the reaction products. The simultaneous measurements of both the analyte(s) and reaction products using two independent detection mechanisms can improve both the selectivity and reliability.

Mode 2: Applying Electrochemical Gate Potential

In this mode, the electrochemical gate potential is swept within a desired range to monitor the both the drain current and the electrochemical potential of the conductive material in junction 145. This same potential is applied to the working electrode 130 to produce the electrochemical reaction with analyte(s) 107 as well as to monitor the electrochemical activity in a potential range due to the redox properties of analyte(s) 107 as well as the reaction products. The same potential window size can be applied, but the potential window can be shifted to a range relevant for the electrochemical reaction of interest to take place. This range can be different than the potential range of the junction electrochemistry.

In both Mode 1 and Mode 2, optical sensor 170 detects analyte(s) 107 or their reaction products generated by the electrochemical potentials. Also, in both Mode 1 and Mode 2, instead of controlling the potential and detecting the current, one can also control the current and detect the potential.

In each mode described above, it is possible to detect analytes and reaction products based on the following different sensing mechanisms described below.

Case A: EC Assisted Detection.

In this embodiment, analyte 107 is electrochemically active and its reaction irreversible. When analyte 107 arrives at the surface of third working electrode 130, analyte 107 is reduced or oxidized. When analyte 107 reaches junction 145, it modifies the conductance of junction 145. The changes in drain current (Id) on junction 145 and the electrochemical current on third working electrode 130 are monitored. Analyte(s) 107 or the reaction products can also detected by the optical detection.

Case B: Non-assisted Detection.

In this embodiment, analytes 107 are reduced or oxidized on third working electrode 130, and they interact with the junction 145 directly. The interactions of analyte(s) 107 rather than their reduction products with junction 145 affect the conductance of junction 145. Alternatively, the analyte(s) 107 may change the conductance with the help of a redox mediator or a chemical functionalization of the junction 145 with enzymes, peptides, nucleic acids or functional groups like amides, carboxyl groups and sulfurs. The changes in drain current (Id) of junction 145 and the electrochemical current on third working electrode 130 can also be monitored.

Application to Multiple Analyte Detection in Liquid and Gas Phases

Integration of many sensors can be achieved in on single chip, and simultaneous monitoring of multiple analyte(s) 107 can be potentially achieved by adjusting the chemical modification as well as gated and biased potentials. Detection of analyte(s) 107 in liquid phase involves delivery of the sample through injections to a bath cell or through a microfluidic system, while detection of chemical vapors comprises diffusion gases through a supporting electrolyte layer.

Electrochemical-Optical Embodiments

Figure 10:
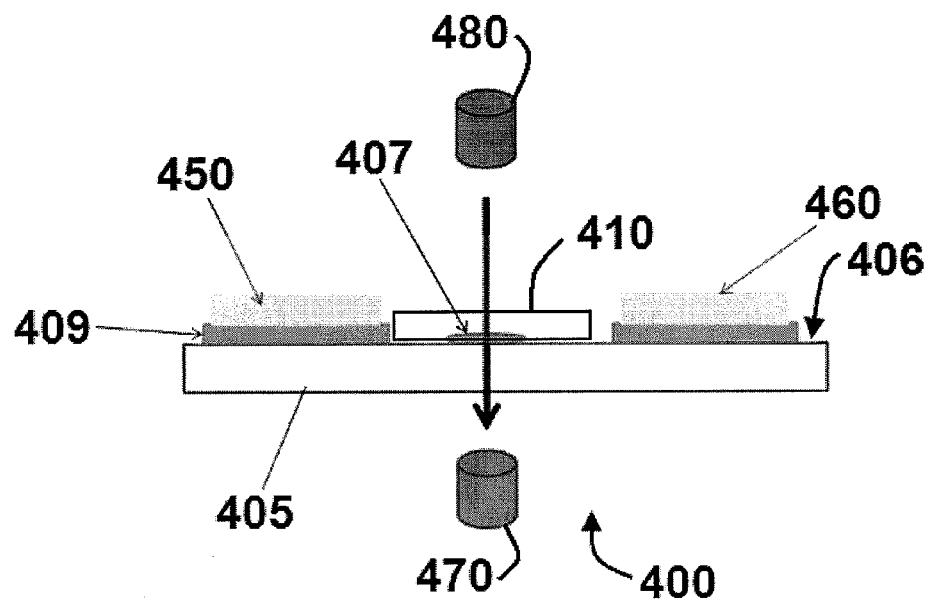
FIG. 10 shows a schematic of a side view of an EC-O sensor with a first configuration for the optical sensor in accordance with embodiments of the present disclosure.
Figure 11:
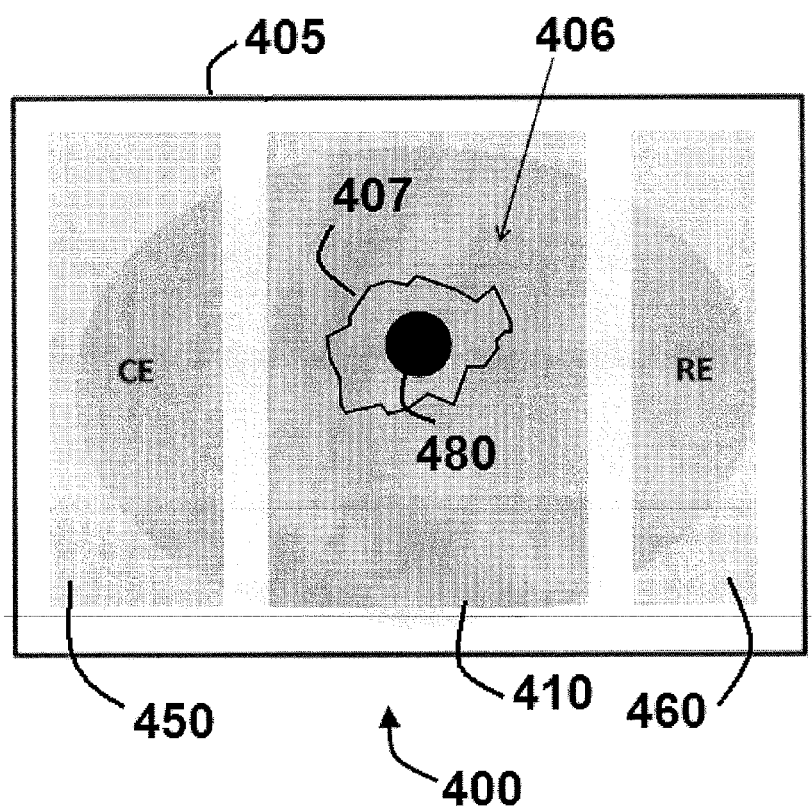
FIG. 11 shows a schematic of a top view of the embodiment of a FIG. 10.

Referring now to FIGS. 10-11, an embodiment of a sensor 400 is shown that provides for detection of electrochemical signals and optical properties of an analyte 407. This embodiment comprises a working electrode 410, as well as a counter electrode 450 and a reference electrode 460 that are supported on a solid state substrate 405 and covered with an electrolyte 406. Electrodes 450 and 460 are isolated from substrate 405 by insulating material 409. In this embodiment, sensor 400 also comprises an optical detection system comprising an optical sensor 470 and a light source 480 that are located on the opposite sides of substrate 405. Sensor 400 operates similar to previously-described embodiments (e.g. sensor 100 in FIGS. 6-7), but is configured to provide electrochemical and optical (EC-O) analysis rather than electrochemical, electrical and optical (EC-E-O) analysis.

Figure 12:
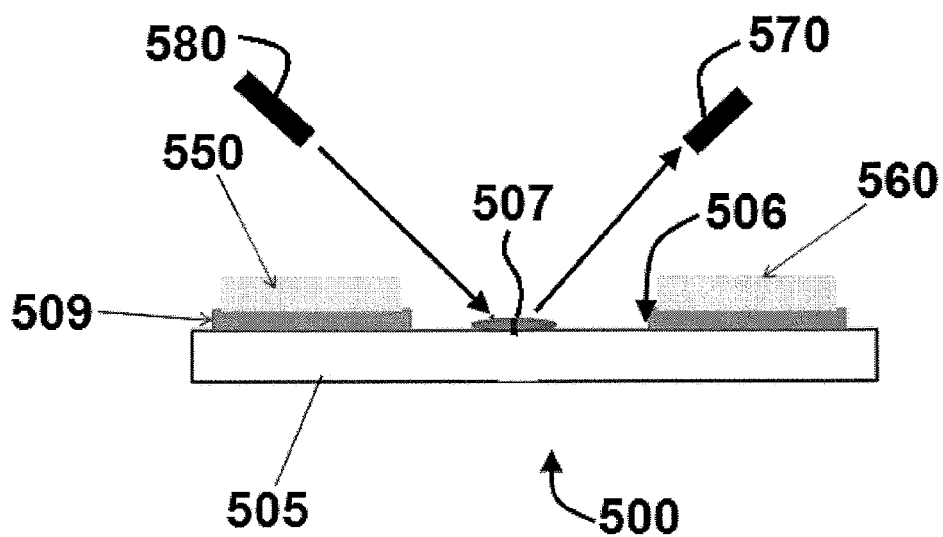
FIG. 12 shows a schematic diagram of a side view of an EC-O sensor with second configuration for the optical sensor in accordance with embodiments of the present disclosure.

FIG. 12 illustrates an embodiment of a sensor 500 is shown that also provides for detection of electrochemical signals and optical properties of an analyte 507. This embodiment comprises a counter electrode 550 and a reference electrode 560 that are supported on a solid state substrate 505 and covered with an electrolyte 506. Electrodes 550 and 560 are isolated from substrate 505 by insulating material 509. In this embodiment, sensor 300 also comprises an optical detection system comprising an optical sensor 570 and a light source 580 that are located on the same side of substrate 505. Sensor 500 operates similar to previously-described embodiments (e.g. sensor 100 in FIGS. 8), but is configured to provide electrochemical and optical (EC-O) analysis rather than electrochemical, electrical and optical (EC-E-O) analysis.

Experimental Results of Exemplary Embodiment

Figure 13:
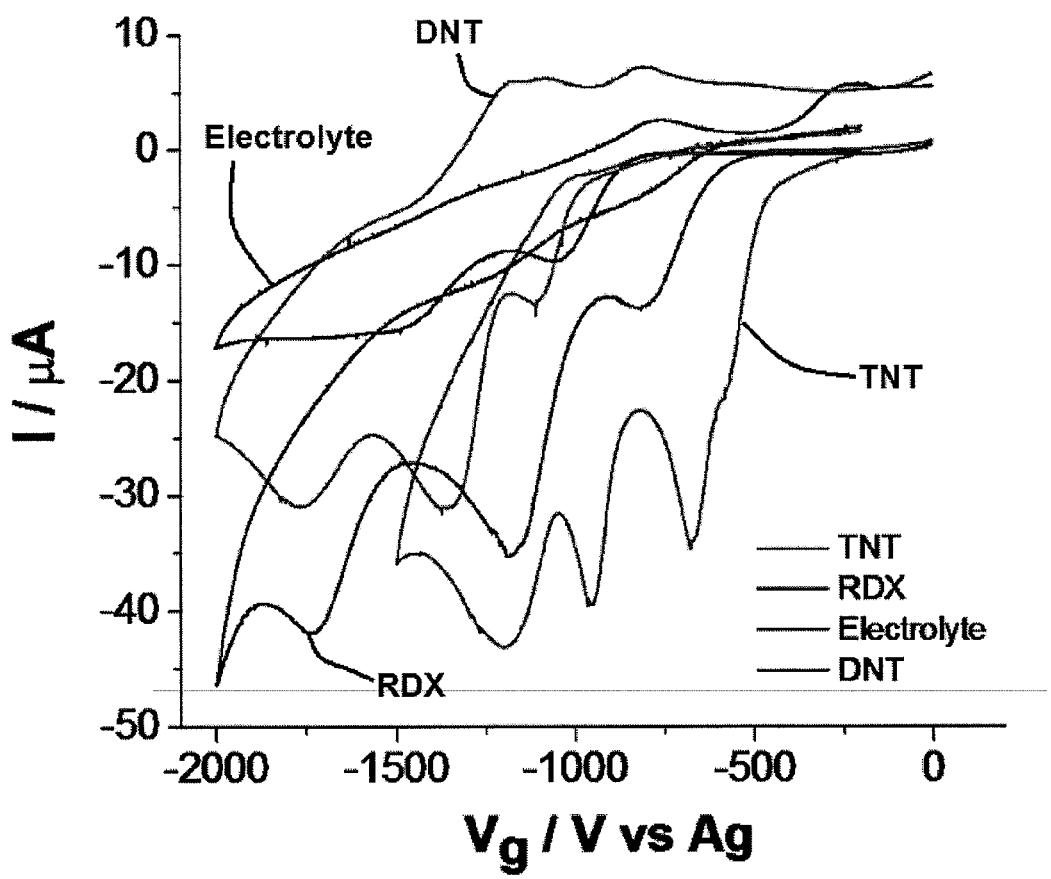
FIG. 13 illustrates a plot of electrochemical current versus potential, in accordance with embodiments of the present disclosure.
Figure 14:
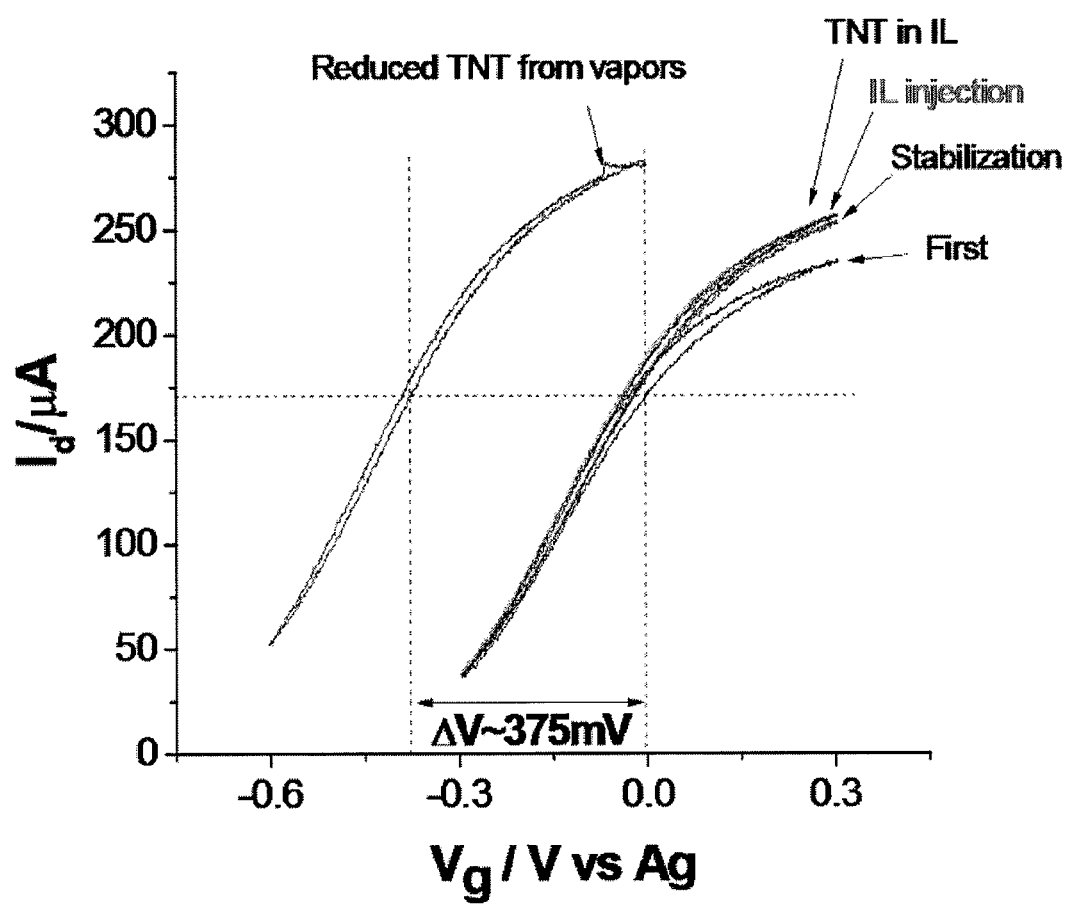
FIG. 14 illustrates a plot of the drain current versus electrochemical gate potential of a conductive material junction, in accordance with embodiments of the present disclosure.
Figure 15:
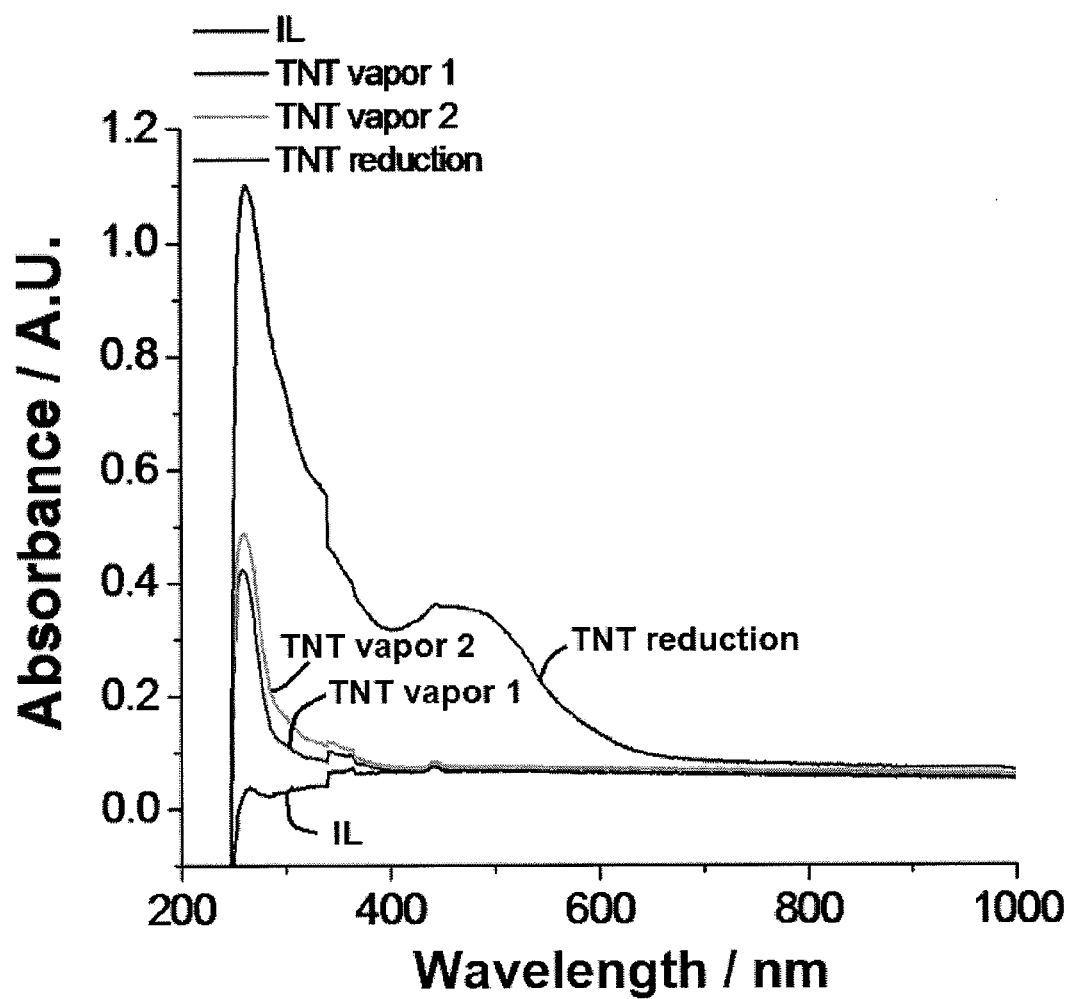
FIG. 15 illustrates a plot of the absorbed light intensity in absorbance units versus the incident light wavelength in nanometers, in accordance with embodiments of the present disclosure.
Figure 16:
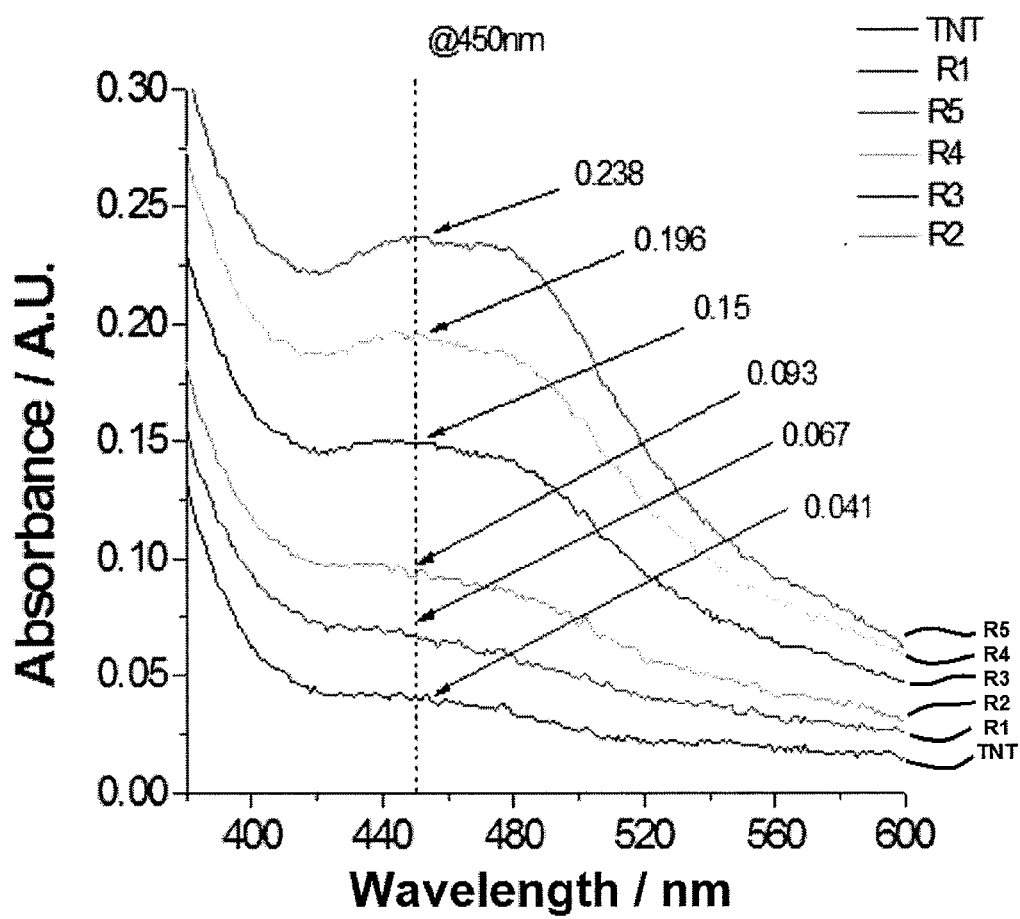
FIG. 16 illustrates a plot of the increasing absorbance with increasing reduction cycles on the working electrode, in accordance with embodiments of the present disclosure.

FIGS. 13-16 show three detection mechanisms used by sensor 100. FIGS. 14-16 also illustrate detection mechanisms that may be used by sensors 200 and 300. FIG. 13 illustrates the electrochemical current vs. potential plot and demonstrates the difference of electrochemical activity for the supporting electrolyte, explosives, such as DNT, TNT and RDX. FIG. 13 illustrates the difference in reduction potentials for different compounds using cyclic voltammetry. The figure shows the electrochemical potential in microamperes versus the applied electrochemical potential ($V_g$)in volts using a Silver (Ag) wire as a reference electrode.

FIG. 14 illustrates the drain current (Id) vs. electrochemical gate potential (Vg) of a conductive material junction 145, in this case a conductive polymer. This figure also shows the shift of the electrochemical potential of around 0.375V due to the interaction with the reduction products created on the third working electrode 130 from TNT vapors. A detection limit in the ppb range has been achieved for TNT. In this plot, silver wire was also used as the reference electrode.

FIG. 15 shows the UV-visible spectra of TNT collected vapors and reduction products collected form TNT vapors, showing an increase in the absorbance at around 450 nm wavelength. The plot shows the absorbed light intensity in absorbance units, versus the incident light wavelength in nanometers. FIG. 16 shows the increasing absorbance with increasing reduction cycles on the working electrode.

Potential Applications

Exemplary embodiment of sensors described in this disclosure may be used to detect various types of analytes. Non-limiting examples of applications for various analytes are provided below.

Hydrogen Gas Detection

Hydrogen gas may be highly selectively detected from electrochemically produced protons from hydrogen oxidation on catalytic materials used as electrode material. The generated protons could be conductimetrically detected in a semi-conducting material across a nanogap when material is sensitive to change in protons and/or colorimetric detected if a redox-sensitive organic molecule is embedded in the supporting electrolyte.

Other Gases

The principle is similar to hydrogen gas detection. However, different catalytic electrode materials can be used to totally or partially direct gas oxidation or reduction in exemplary embodiments. Gases, such as but not limited to NO, CO, $H_2S$, $NH_3$ could be highly selectively detected from electrochemically produced or consumed protons by conductimetric increase or decrease detected in a semi-conducting material across a nanogap and/or by color change through a redox-sensitive organic molecule embedded in the supporting electrolyte. The deconvolution of gases concentration in complex samples could be done by proper materials, potentials and calibration of the system.

Enzymatic Activity Detection

The enzymatic activity of widely used enzymes, such as but not limited to alkaline phophatase, peroxidase, glucose oxidase, copper-based active site enzymes, amylase, etc. could be detected via exemplary embodiments of the sensors described in this disclosure. The enzymes can: (a) catalyze the conversion of enzymatic substrates to products that can be electrochemically oxidized or reduced; or (b) decrease the concentrations of reporters that can be electrochemically transformed.

The electrochemical products can be detected conductimetrically through interaction with the semiconducting material immobilized in the nanogap and/or colorimetric detected because of a change in color from the electrochemical product by: (a) contact with the supporting electrolyte; (b) contact with an additive embedded in the supporting electrolyte; and/or (c) further electrochemical oxidation/reduction.

Non-limiting examples include detection of enzymes typically used in immunologic ELISA assays. The detection methods can bring higher selectivity and sensitivity and may avoid use of typically chromogenic additives bringing economic and environmental. Other examples of use are enzymes of clinical or biological importance such but not limited to alkaline phosphatase and amylase.

Ketones and Aldehydes Derivatives

In certain embodiments, detection of ketones and aldehydes such as but not limited to acetone, acetaldehyde can be performed by use of supporting electrolytes embedded with hydroxylamines or hydrazines. Reaction products of the analytes with the reagents can be detected electrochemically and colorimetrically and/or conductimetrically.

Heavy Metal Ions

In certain embodiments, heavy metal ions can be detected by modification of electrodes and/or conducting bridge or supporting electrolytes with a recognizing element based on organic molecule, biomimic or biological component. The recognizing element: (1) on the electrode can act as preconcentrator of the heavy metal ions that can be electrochemically reduced; (2) on the conductive material bridge can induce conformational, charge or pH changes that are transduced as a change in conductance; (3) in the supporting electrolyte can induce change in distinctive changes in color upon analyte injections or after re-oxidation previous reductive-preconcentration on a working electrode.

All of the methods disclosed and claimed herein can be executed without undue experimentation in light of the present disclosure. While the methods of this disclosure may have been described in terms of preferred embodiments, it will be apparent to those of ordinary skill in the art that variations may be applied to the methods and in the steps or in the sequence of steps of the method described herein without departing from the concept, spirit and scope of the disclosure. All such similar substitutes and modifications apparent to those skilled in the art are deemed to be within the spirit, scope, and concept of the disclosure as defined by the appended claims.

The following example is included to demonstrate specific embodiments of this disclosure. It should be appreciated by those of skill in the art that the techniques disclosed in the example that follows represent techniques discovered by the inventors to function in the practice of the invention, and thus can be considered to constitute specific modes for its practice. However, those of skill in the art should, in light of the present disclosure, appreciate that many changes can be made in the specific embodiments which are disclosed and still obtain a like or similar result without departing from the scope of the invention.

Figure 17:
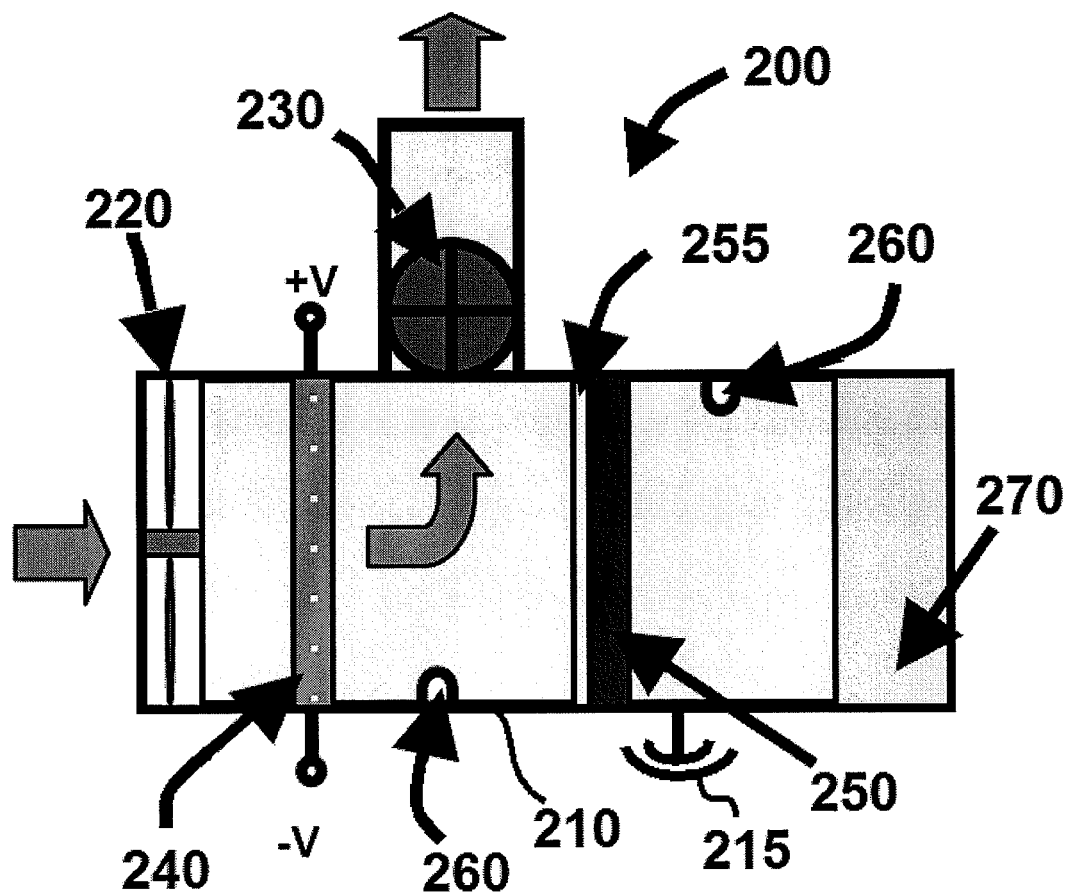
FIG. 17 illustrates a schematic diagram of a side view of a sensor in accordance with embodiments of the present disclosure with an outlet valve in the open position.
Figure 18:
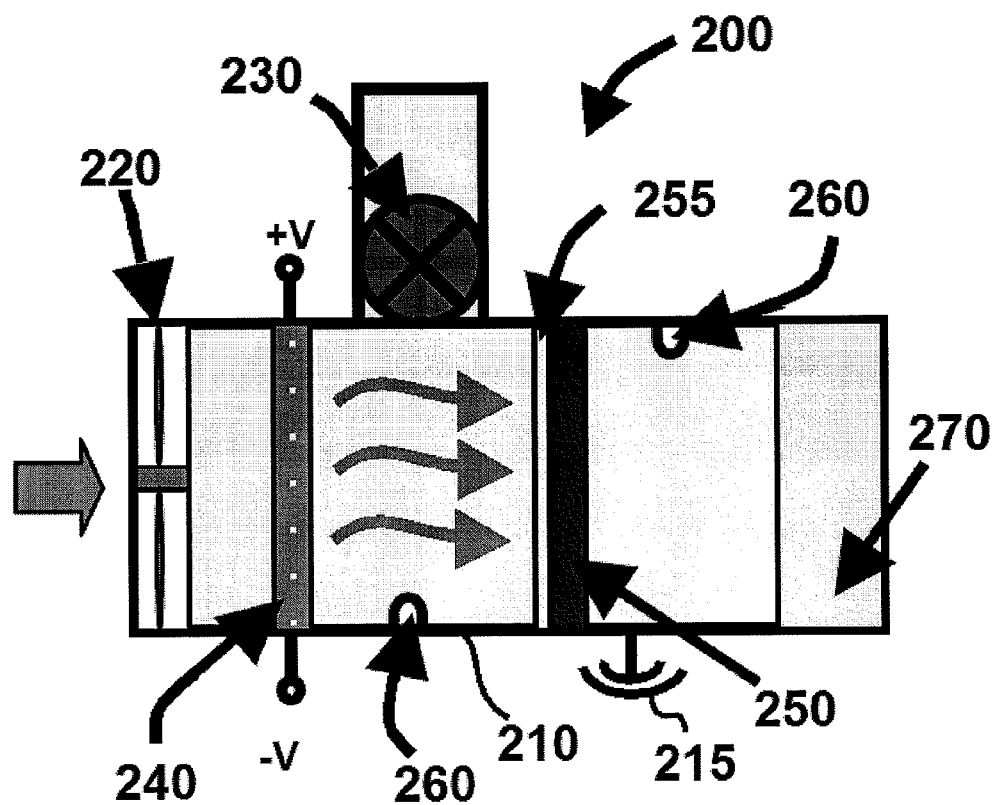
FIG. 18 illustrates a schematic diagram of the embodiment of FIG. 14 with the outlet valve in the closed position.
Figure 19:
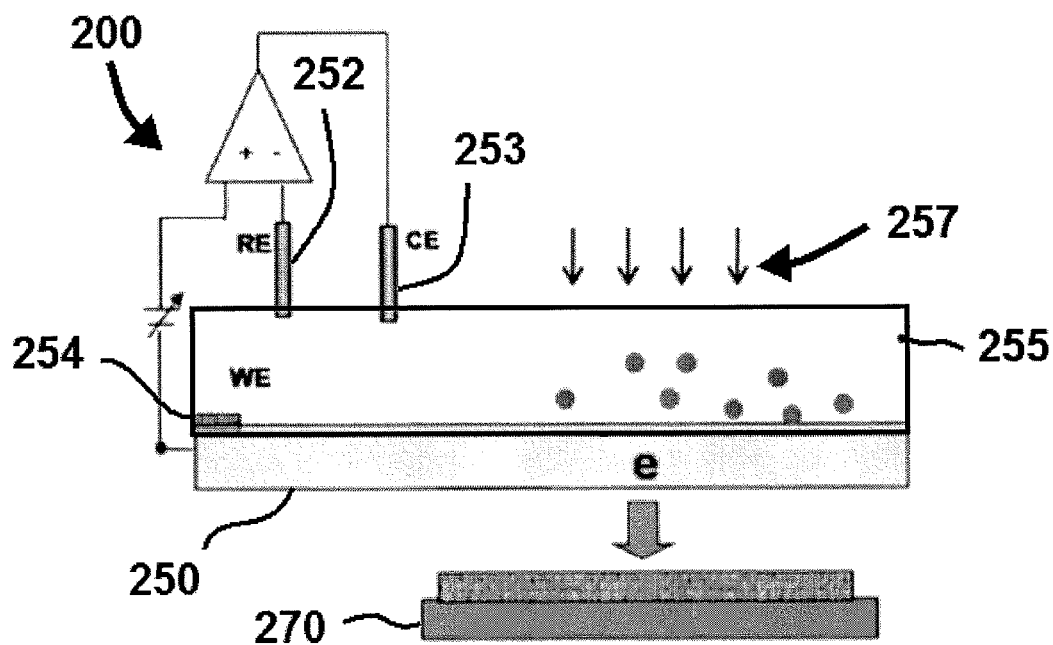
FIG. 19 illustrates a schematic diagram of components of the embodiment of FIG. 14.

A schematic of a sensor system 200 is shown in FIGS. 17 and 18, while a more detailed view of a sensor utilized in sensor system 200 is shown in FIG. 19. In the embodiment shown, sensor system 200 utilizes electrochemical, chemical, and optical properties of analytes (including e.g., explosives) in a thin film of ionic liquid that provides a conductive matrix. In certain embodiments, the ionic liquid can be 1-butyl-3-methylimidazolium hexafluorophosphate (BMIM-$PF_6$).

In the exemplary embodiment shown, sensor system 200 comprises a housing 210, an air sample delivery system or fan 220, an outlet valve 230, a filter/heater 240, a sensor substrate 250 with an ionic liquid film 255, a light source 260 and an optical detector 270.

A brief overview of the operation of system 200 will be provided initially, followed by a more detailed discussion of specific features. During operation, fan 220 (or a similar air mover) draws air from the outside environment into housing 210. Upon entry into housing 210, the air can be filtered by filter/heater 240. In the initial stages of operation, outlet valve 230 is in an open position to allow air to flow out of housing 210. This can allow a large volume of air to be passed through filter/heater 240 and increase the amount of analyte material that is captured by filter 240. Fan 220 can be operated with outlet valve 230 in the open position for a period of time to allow a sufficient amount of analyte to be captured by filter/heater 240.

After a sufficient amount of analyte has been retained by filter/heater 240, outlet valve 230 is moved to the closed position as shown in FIG. 18. With outlet valve 230 closed, filter/heater 240 can be turned on to heat the analyte material captured by filter/heater 240. In specific embodiments, filter/heater 240 comprises a mesh material and a heater is embedded in filter/heater 240. In certain embodiments, the heater can be heated to a temperature slightly above the boiling point of the analyte (but not to a temperature high enough to cause decomposition of the analyte materials). In specific embodiments, when valve 230 is closed and the heater is activated, fan 220 may be operated in a low flow mode (e.g. at a rate that produces a lower air flow than when valve 230 is open). This can direct vapors resulting from the heated analyte materials towards ionic liquid 255, rather than allowing the vapors to migrate back across fan 220 and out of housing 210. Allowing the analyte vapors to stay longer in the headspace of ionic liquid 255 can allow ionic liquid 255 to further selectively concentrate the analyte vapors, as explained in more detail below.

Referring now to FIG. 19, sensor substrate 250 comprises a reference electrode 252, a counter electrode 253, and a working electrode 254. In specific embodiments, ionic liquid 255 can coat one or more of the electrodes. In specific embodiments, the coating can be approximately 30-40 µm thick. A potential can be applied across one or more of the electrodes (in a manner similar to previously described embodiments) and an electrochemical reaction can be measured (e.g., via a cyclic voltammogram) to determine an analyte 257. In certain embodiments, the potential may controlled via a microcontroller-based potentiostat (not shown for purposes of clarity).

As described in more detail below, ionic liquid 255 can serve multiple beneficial purposes, including for example: (1) a medium that selectively preconcentrates analytes and quickly transports the analytes to the electrodes, (2) an electrolyte that is highly stable under ambient conditions for electrochemical reactions, and (3) a medium that promotes the formation of colored reduction products.

Figure 20:
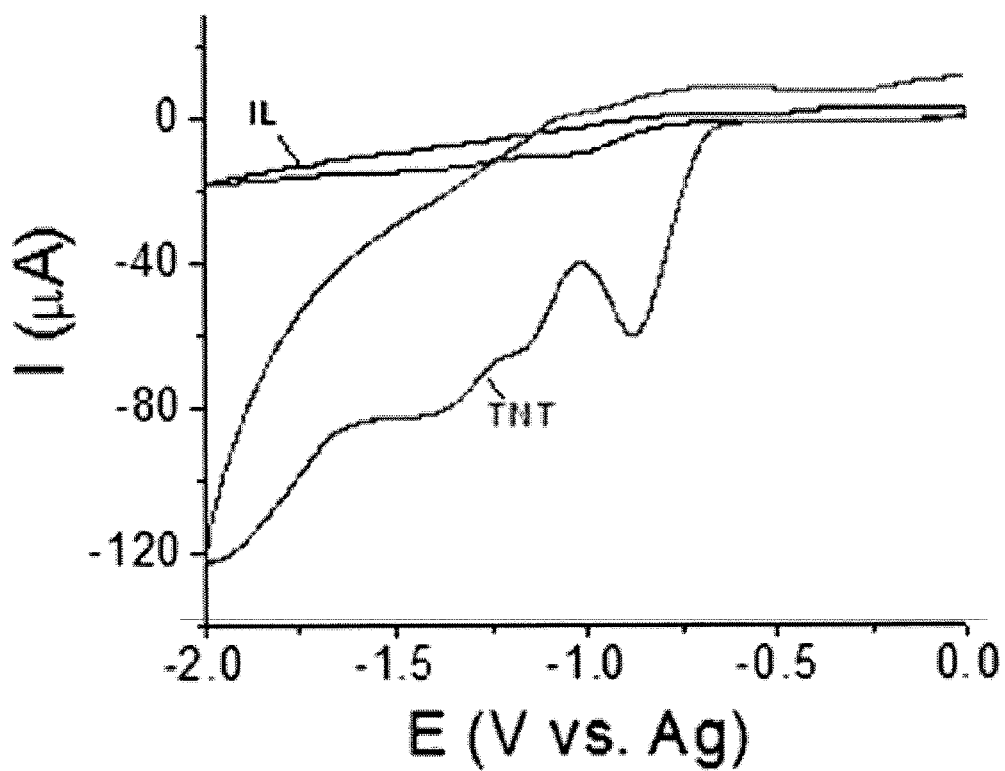
FIG. 20 illustrates a plot of electrochemical current versus potential for a first analyte, in accordance with embodiments of the present disclosure.
Figure 21:
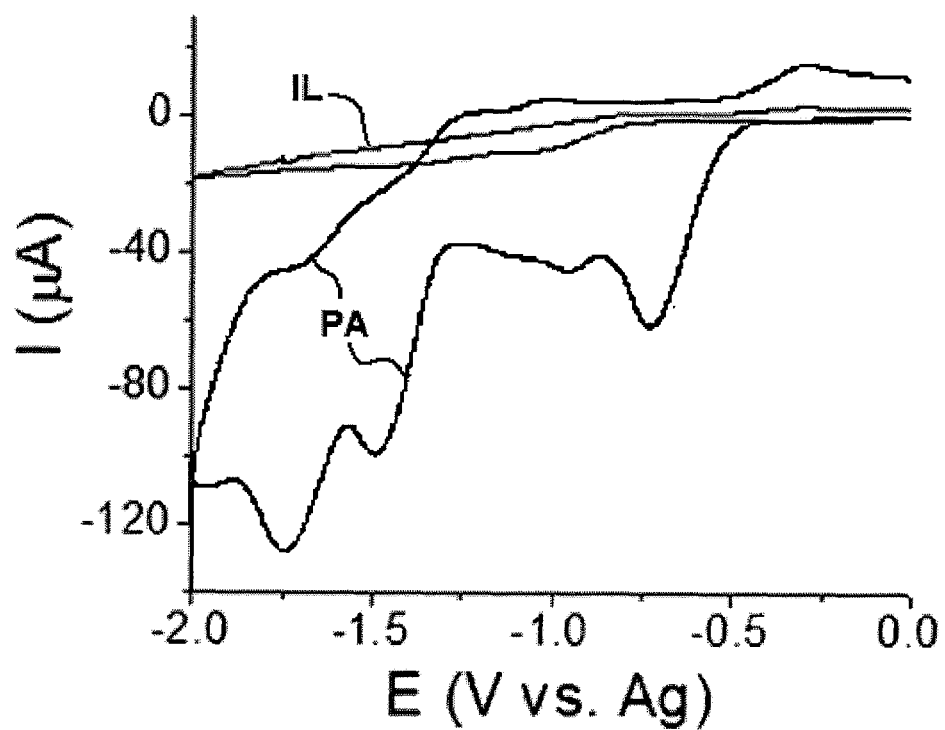
FIG. 21 illustrates a plot of electrochemical current versus potential for a second analyte, in accordance with embodiments of the present disclosure.
Figure 22:
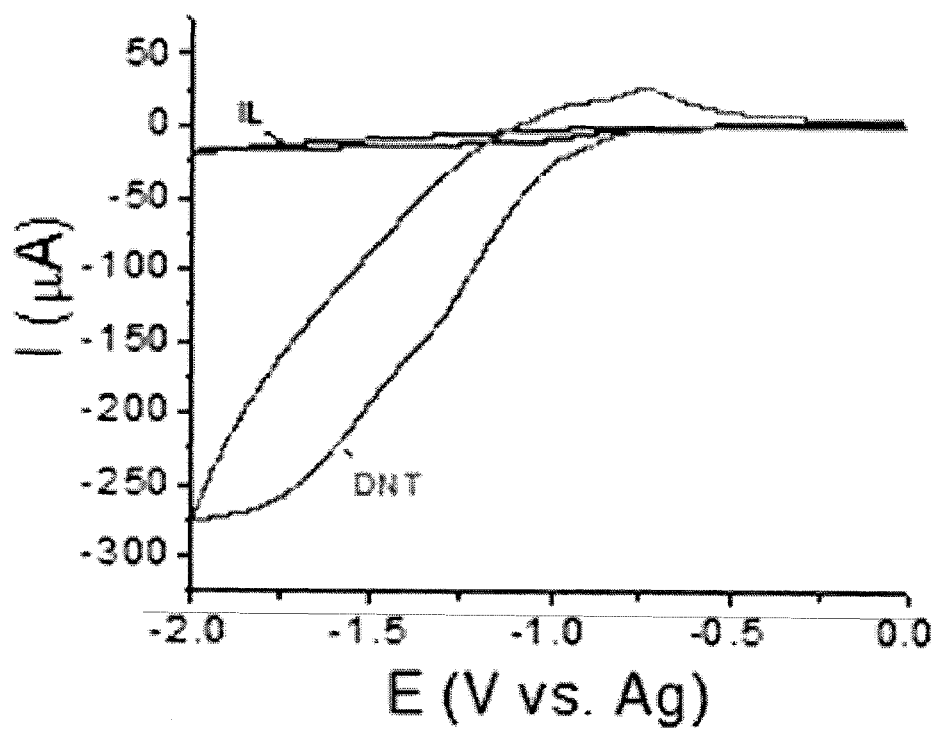
FIG. 22 illustrates a plot of electrochemical current versus potential for a third analyte, in accordance with embodiments of the present disclosure.

FIG. 20 illustrates a cyclic voltammogram of an ionic liquid (BMIM-PF$_6$) without the presence of the analyte (noted with the marking "IL") and with the presence of an analyte (in this example, 2,4,6- trinitrotoluene, noted as "TNT"). In the example shown, gold electrodes were utilized at 100 mV/s. FIG. 21 provides a similar cyclic voltammogram with picric acid (PA), while FIG. 22 provides a similar cyclic voltammogram for 2,4-dinitrotoluene (DNT).

In addition to electrochemical reactions, the interactions of the analyte and the ionic liquid under the applied potential can produce reaction products that can be illuminated with light source 260 and optically detected by optical detector 270. In specific embodiments, light source 260 is a light-emitting diode (LED) and optical detector 270 is a complementary-metal oxide sensor (CMOS) camera. The embodiment shown in FIGS. 14 and 15 comprises a light source 260 on each side of sensor substrate 250. Other embodiments may comprise a light source on only one side of sensor substrate 250. In certain embodiments sensor substrate 250 comprises a transparent substrate of indium tin oxide (ITO) with printed electrodes.

Figure 23:
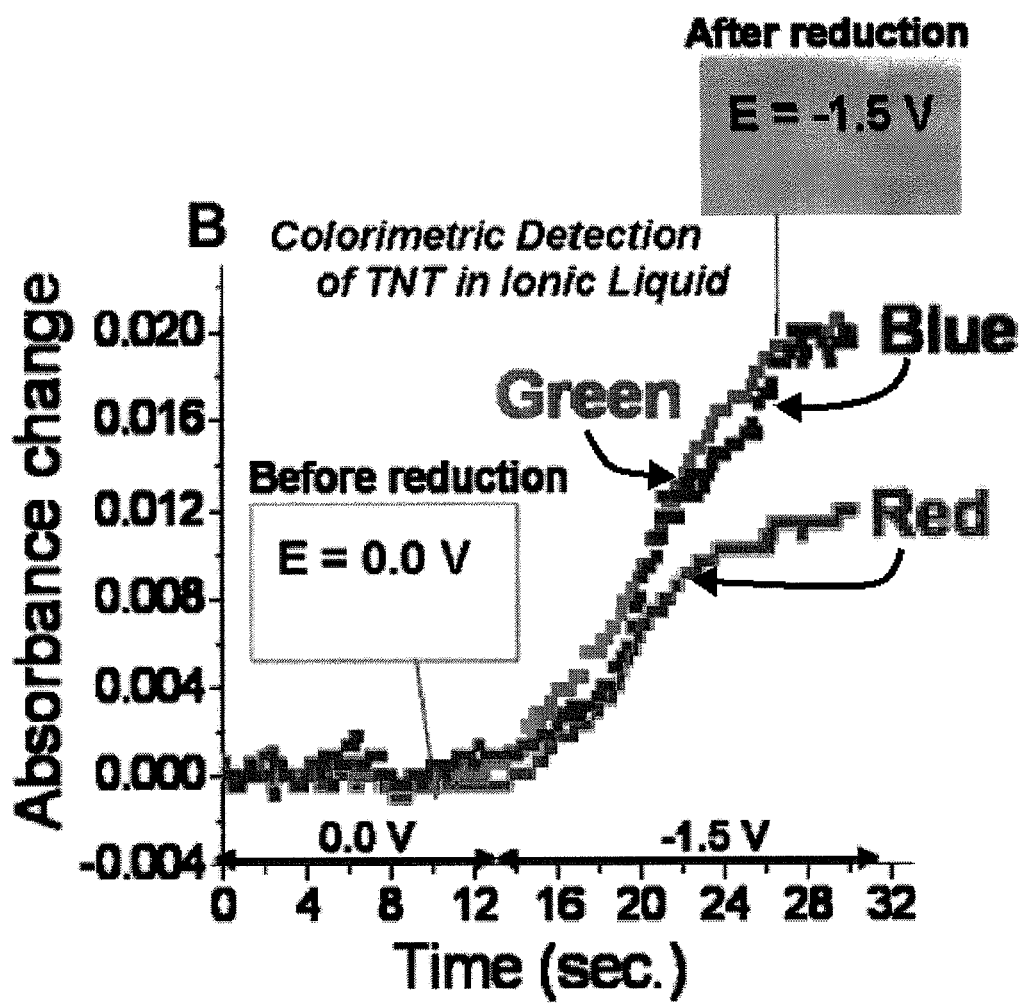
FIG. 23 illustrates a plot of absorbance change for red, green and blue colors for an analyte in an ionic liquid, in accordance with embodiments of the present disclosure.
Figure 24:
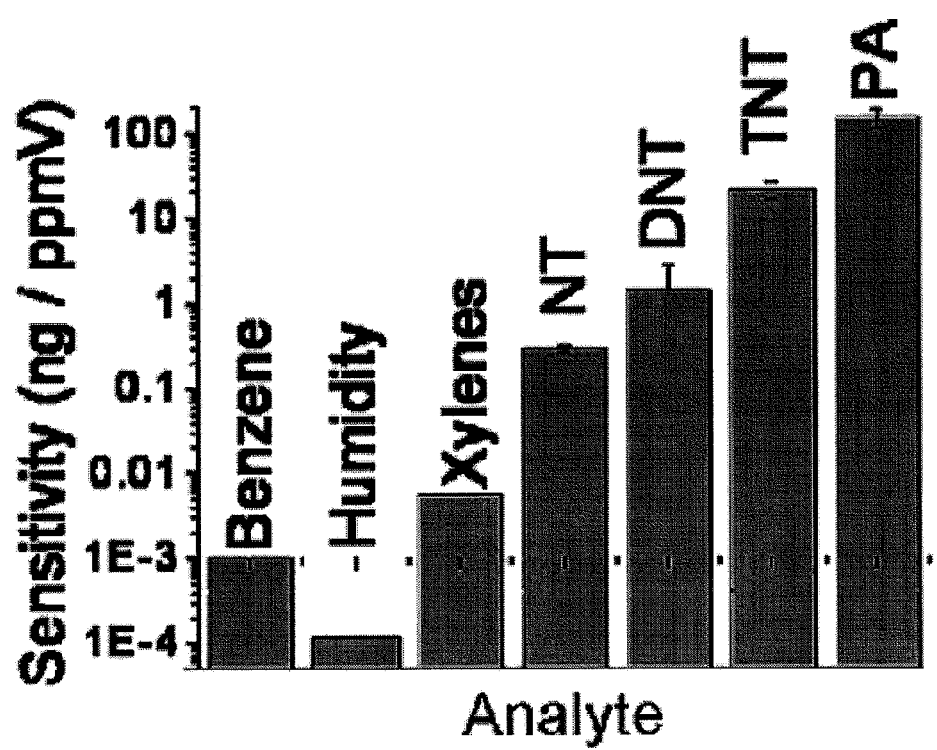
FIG. 24 illustrates a plot of the preconcentration capacities of various analytes.
Figure 25:
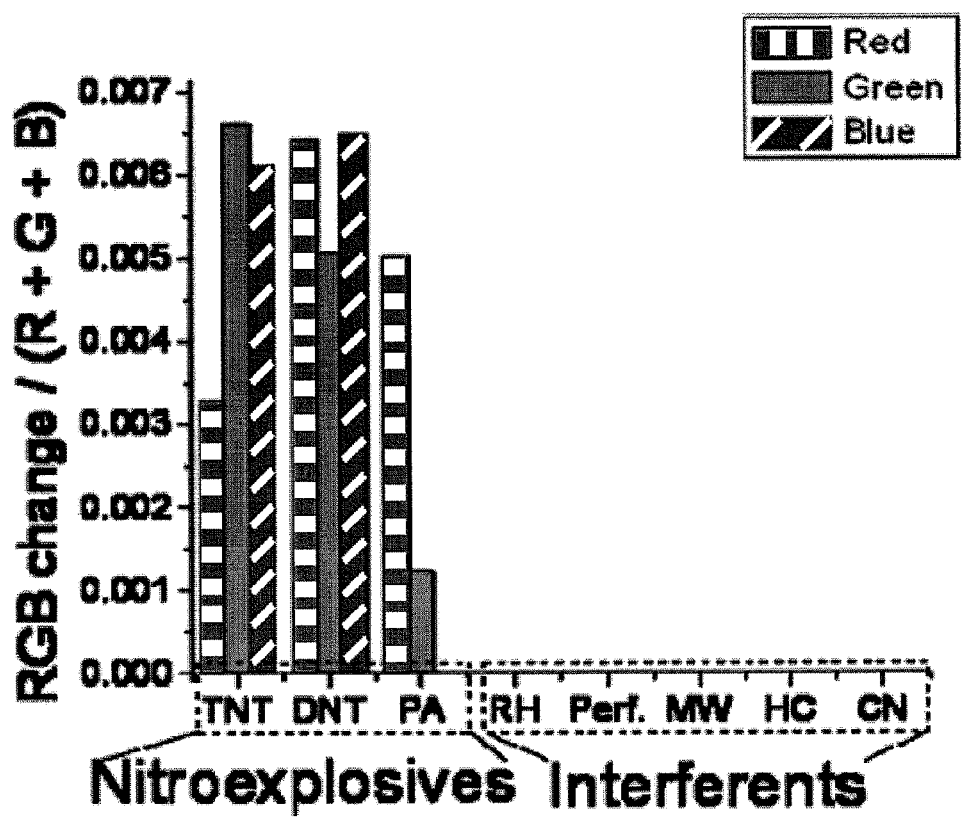
FIG. 25 illustrates the red, green and blue (RGB) color changes for various analytes, including nitroexplosives, and interferents, in accordance with embodiments of the present disclosure.

As shown in FIG. 23, the reduction processes produce distinctive red colored products. The absorbance change for each color is defined as the logarithmic ration of the intensity in a sensing area (e.g., working electrode) to the intensity in a reference area (e.g., reference electrode). The absorbance change shown in FIG. 23 and the electrochemical responses shown in FIGS. 20-22 provide unique markers that can be used to determine the identity of the analyte. Referring now to FIG. 24, the preconcentration capacities of various analytes in BMIM-PF$_6$ are shown, including benzene, water, xylene, nitrotoluene (NT), 2,4-dinitrotoluene (DNT), TNT, and picric acid (PA). FIG. 25 illustrates the red, green and blue (RGB) color changes for various analytes, including nitroexplosives, and interferents. As shown, the color changes for the nitroexplosives (TNT, DNT and PA) was much greater than that of the interferents. The interferents measured included water vapor (specifically, an increase in relative humidity of 21%, denoted by "RH" in the graph), a common perfume (denoted by "Perf."), a mouthwash ("MW"), hydrocarbons including a hexane/toluene mixture ("HC"), and a general cleaner ("CN").

Figure 26:
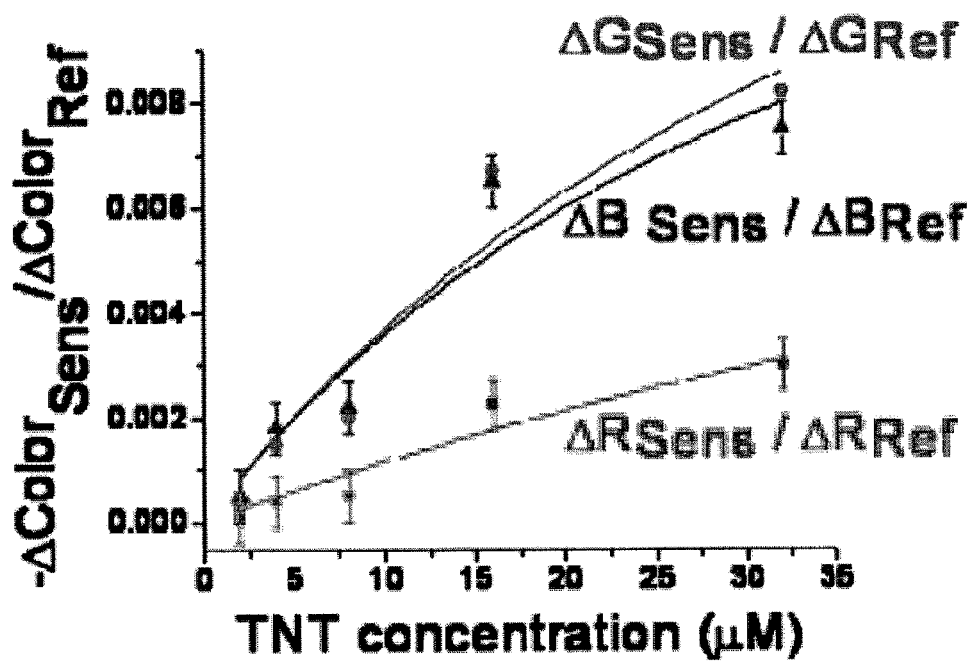
FIG. 26 illustrates a plot of the total color change on a sensing area normalized by the color change of a reference area as a function of analyte concentration, in accordance with embodiments of the present disclosure.

In addition, the data show distinct color patterns for different nitroexplosives, allowing us to identify different nitroexplosives. Additional discrimination can be achieved by controlling the electrochemical potential because different analytes have different electrochemical activities. Furthermore, discrimination can be achieved by following the kinetics of the color changes due to the different reaction mechanisms. The total color change on a sensing area normalized by the color change of a reference area can be determined as a function of analyte concentration and observed a quasi linear dependence, as shown in FIG. 26. Such data can be used for quantitative detection of explosives.

In certain embodiments, sensor 200 may comprise a wireless transmitter 215. Wireless transmitter 215 can allow sensor 200 to communicate with other data collection devices. In a specific embodiment, sensor 200 may be part of an ad hoc wireless sensor network that can be useful in situations where multiple sensors are needed to monitor a variety of different environments.

In a specific example, sensor 200 may be used as part of an ad hoc wireless sensor network to monitor cargo containers. Unfortunately, most freight or cargo containers are made of metal, and metal sheets tend to block radio waves. Surrounding containers can cut off electromagnetic signals needed for communication, making a typical single base station type communication ineffective. Additionally, other issues such as interference with another source and multi-path interferences can further complicate communication between a sensor and other information-gathering devices. If a path of the radio wave for a data link is blocked, communication with the sensor modules can be lost, necessitating personnel to be dispatched to fix the problem. Further complications may arise when some of the containers may be destined to be unloaded at certain ports along the way while others may have to be loaded at certain ports along the way. With thousands of freight containers stacked together, it is not hard to understand why the transportation industry is so reluctant to screen all of cargo containers. If continuous monitoring is required, it can present difficult logistic issues.

Figure 27:
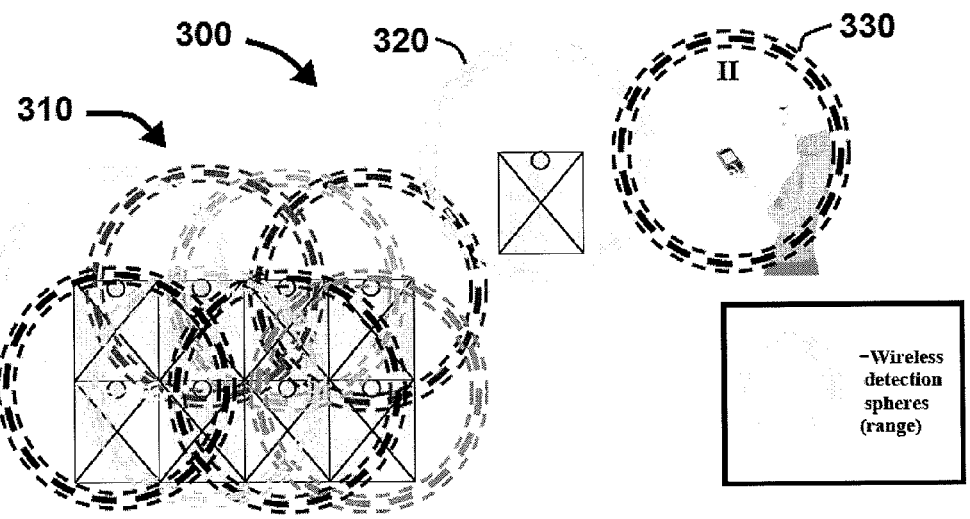
FIG. 27 illustrates a schematic of a wireless network, in accordance with embodiments of the present disclosure.

In an exemplary embodiment shown in FIG. 27, a wireless sensor network 300 can be utilized to address the above challenges. In the specific embodiment shown, wireless network 300 is a proximity-sensing, self-constructing ad hoc wireless network. A viable link can be established via a daisy-chain wireless link as long as the wireless detection spheres 310 (e.g. the region where communication can be established with the wireless device in question) of the sensor modules' wireless units can form a data bridge from the module to the detection sphere 320 of the monitoring system. Detection spheres 310 extend around each sensor 200 and wireless transmitter 215 (not labeled for purposes of clarity).

In certain embodiments, the monitoring system will be frequently finding data routes to access all sensor modules. Since the amount of information transmitting from an individual sensor module is very little, there will be significant inactive time that can be spent on route finding a data relay, even with thousands of containers. The advantages of exemplary monitoring systems utilizing wireless networks include, for example: (1) low power as the transmitter-to-receiver distances are reduced; (2) the metal containers blocking the radio frequency signal can become a much lesser problem since the network works on a relay scheme (using individual sensor nodes as bridges), and the communication path can meander and reach hard to reach places, even places where direct radio signal from a central transmitter would not reach; (3) the wireless network is inherently flexible in its construction, and containers do not have to be arranged in a specific manner to accommodate the network; (4) the wireless network can automatically find alternate routes if there is any communication issues (e.g., network self-healing), thus reducing the chance of a broken communication; (5) the system can automatically track containers simplifying the logistics of loading and unloading, and; (6) if desired, an inspector can also remotely access the status of particular container with a portable device without having to open it, thus reducing the risk for the operator and potentially preventing sensitive cargos from getting damaged (such as perishable food, etc.).

The hybrid sensor together with the preconcentrator, described above, can provide selective and sensitive detection of traces of explosives. However, to develop a truly practical detector system for cargo container security applications, there are other key issues that have to be considered. A modern freight carrying vessel can carry typically more than 1000 containers, with the largest vessel being able to carry more than 8000 freight containers.[15] For 100% screening, it will be a very labor-intensive task to check the status of the sensor in each container. This onerous task can be readily avoided by employing some sort of network connecting the containers to a central monitoring server. However, a wired network will add cumbersome fixed infrastructure on the ship and requires every container to be plugged in, thus adding work to load containers. To mitigate this need, a wireless network is a logical choice.

In certain embodiments, additional fans or air moves can be installed inside a container to ensure adequate air flow inside the container to carry explosive vapors/particulates to the sensor inlet. It is desired to have the explosives vapors/particulates reach the sensor substrate and ionic liquid rather than adhere to other surfaces. In certain embodiments, the sensor module should also be located in the container to sample and capture explosives vapors and particulates from packed hidden explosives. After the analytes are released from the preconcentrator portion of the sensor module and are detected by the sensor, the sensor data can then be processed and a "Go/No Go" signal along with measurement time stamp can be sent out via the established data link.

In certain embodiments, while the wireless unit is not sending out data, it can be either in sleep mode to save power, establishing data links with other modules, or relaying data from other modules. Results from all sensor modules can be collected by an automated centralized one-stop monitoring server. If there is a positive detection, the operator can be notified with the container identification number via either the system display or be wirelessly notified with a portable device such as a cell phone.

The invention claimed is:

1. A sensor comprising:
   a first electrode disposed on a substrate;
   a second electrode disposed on the substrate and spaced apart from the first electrode;
   a coupler coupling the first electrode to the second electrode;
   an electrolyte;
   a counter electrode;
   a reference electrode;
   wherein at least one of the electrodes is connected to an electronic circuit for electrochemical-electrical control and/or measurement during use and wherein an analyte is sensed by determining a change in conductance and/or a change in electrical current; and
   an optical detection system including a light source and an optical detector positioned to receive optical signals from an analyte during use.

2. The sensor of claim 1 wherein the light source is a light-emitting diode.

3. The sensor of claim 1, wherein the light source is located on one side of the substrate and the optical detector is located on an opposite side of the substrate from the light source.

4. The sensor of claim 3, wherein the optical detector is configured to receive light transmitted from the light source and through the substrate and an analyte and its reaction products during use.

5. The sensor of claim 1, wherein the light source and the optical detector are located on the same side of the substrate.

6. The sensor of claim 5, wherein the optical detector is configured to receive light transmitted from the light source and reflected off of the substrate and an analyte during use.

7. The sensor of claim 1, wherein the optical detector is configured to receive light transmitted from the light source and through a wave guide during use.

8. The sensor of claim 1 wherein the optical detector is selected from the group consisting of:
   a complementary metal-oxide-semiconductor (CMOS) sensor, a color sensor, a photodiode, and a charge-coupled device (CCD).

9. The sensor of claim 1, wherein the first electrode is connected to an electronic circuit for applying a potential perturbation to the first electrode during use.

10. The sensor of claim 9, wherein the electronic circuit is a biopotentiostat.

11. The sensor of claim 1, wherein the counter electrode is disposed on the substrate.

12. The sensor of claim 1, wherein the reference electrode is fabricated on the substrate.

13. The sensor of claim 1, wherein the coupler is disposed on the substrate.

14. The sensor of claim 1, where a surface area ratio between the second electrode and the first electrode allows an electrochemical process taking place on the second electrode and electrical properties between the first and second electrodes to be controlled and/or measured simultaneously.

15. The sensor of claim 1 wherein the coupler includes a semiconductor material.

16. A sensor comprising:
a first electrode disposed on a substrate;
a second electrode disposed on the substrate and spaced apart from the first electrode;
a third electrode placed apart from the first and second electrodes;
a coupler coupling the first electrode to the second electrode;
an electrolyte;
a counter electrode;
a reference electrode; and
wherein at least one of the electrodes is connected to an electronic circuit for electrochemical-electrical control and/or measurement during use and wherein an analyte is sensed by determining a change in conductance and/or a change in electrical current.

17. The sensor of claim 16, wherein the third electrode is configured for electrochemical control and/or measurement during use.

18. The sensor of claim 17, wherein the third electrode comprises a larger surface area than the first and second electrodes.

19. The sensor of claim 16, wherein the first and second electrodes are configured for conductance measurement during use.

20. The sensor of claim 16, wherein the electronic circuit is a tripotentiostat.

21. A sensor comprising:
a first electrode disposed on a substrate;
a second electrode disposed on the substrate and spaced apart from the first electrode;
a coupler coupling the first electrode to the second electrode;
an electrolyte, wherein the electrolyte is an ionic liquid;
a counter electrode;
a reference electrode; and
wherein at least one of the electrodes is connected to an electronic circuit for electrochemical-electrical control and/or measurement during use and wherein an analyte is sensed by determining a change in conductance and/or a change in electrical current.

22. The sensor of claim 21 wherein the first and second electrodes are indium tin oxide (ITO) electrodes and wherein the ionic liquid is disposed over electrodes.

23. The sensor of claim 21, wherein the ionic liquid is 1-butyl-3-methylimidazolium hexafluorophosphate.

24. The sensor of claim 21, further comprising an air sample delivery system.

25. The sensor of claim 24 wherein the air sample delivery system is configured to direct air towards the substrate.

26. The sensor of claim 21 further comprising a wireless transmitter.

27. The sensor of claim 26 wherein the wireless transmitter is a component in an ad hoc wireless network.

28. A method comprising:
providing a sensor having
a first electrode disposed on a substrate;
a second electrode disposed on the substrate and spaced apart from the first electrode;
a coupler including a semiconductor material coupling the first electrode to the second electrode;
an electrolyte consisting essentially of an ionic liquid adapted to receive an analyte in a gas phase or a liquid phase;
a counter electrode;
a reference electrode;
wherein at least one of the electrodes is connected to an electronic circuit for electrochemical-electrical control and/or measurement during use:
providing an analyte;
detecting a reaction product;
determining a conductance and/or electrical current of the conducting or semiconducting material;
determining an electrochemical signal;
determining an optical property of the analyte and/or reaction product; and
detecting the analyte employing the conductance, the electrochemical signal, or the optical property.

29. The method of claim 28, wherein the conductance and/or electrical current is measured using the first electrode.

30. The method of claim 28, wherein the electrochemical signal is measured using the second electrode.

31. The method of claim 28, further comprising adjusting a surface area ratio between the second electrode and the first electrode to optimize performance of the EC-E sensor.

32. The method of claim 28, wherein the analyte comprises a molecule in gas phase.

33. The method of claim 28, wherein the analyte comprises a molecule in liquid phase.

34. A sensor comprising:
an electrolyte consisting essentially of an ionic liquid adapted to receive an analyte in a gas phase or a liquid phase;
a first electrode coupled to the electrolyte;
a second electrode coupled to the electrolyte;
a device configured to apply a voltage between the first and second electrodes, wherein during use the voltage induces an electrochemical reaction on the first electrode and the electrochemical reaction on the first electrode causes a change in an optical property of the electrolyte; and
an optical system configured to measure color changes in the optical property of the electrolyte.

35. A method comprising:
providing a sensor having
an electrolyte consisting essentially of an ionic liquid adapted to receive an
analyte in a gas phase or a liquid phase;
a first electrode coupled to the electrolyte; a second electrode coupled to the electrolyte;
a device configured to apply a voltage between the first and second electrodes, wherein during use the voltage induces an electrochemical reaction on the first electrode and the electrochemical reaction on the first electrode causes a change in an optical property of the electrolyte; and
an optical system configured to measure color changes in the optical property of the electrolyte;
providing an analyte;
detecting a reaction product;
determining an electrochemical signal;
determining a color change of the analyte or reaction product; and
detecting the analyte employing the optical property and the electrochemical signal.

36. The sensor of claim 35 where the analyte is a selected from the group consisting of:
nitroaromatics such as trinitrotoluene (TNT), dinitrotoluene (DNT), picric acid (PA); nitramines such as cyclotrimethylenetrinitramine (RDX), octogen (HMX), Trinitrophenyl-n-methylnitramine (tetryl), nitroesters such as nitroglycerine (NG), ethylene glycol dinitrate (EGDN), Pentaerythritol tetranitrate (PETN); nitrocompounds such as nitromethane; nitrates such as urea nitrate, and tagging agents such as dimethyldinitrotoluene, nitrobenzene, nitrotoluene and their derivatives.

37. The sensor of claim 35, wherein the electrolyte is supported on a substrate.

38. The sensor of claim 37, wherein the substrate is a transparent or semitransparent material.

39. The sensor of claim 37, wherein the substrate is flat and reflective.

40. The sensor of claim 37, wherein the substrate is ITO (Indium-Tin-Oxide), and wherein the substrate is configured to serve as the first electrode and as an optical window in the optical system.

41. The sensor of claim 35, wherein the electrolyte contains one or more additives to enhance the penetration or solubility or chemical reaction of an analyte into the electrolyte and/or the electrochemical reaction.

42. The sensor of claim 35, wherein the electrolyte is an ionic liquid including an imidazolium derivative or an organic solvent with salts.

43. The sensor of claim 42 wherein the imidazolium derivative is 1-butyl-3- methylimidazolium hexafluorophosphate.

44. The sensor of claim 35, further comprising a third electrode configured to control the voltage between the first and second electrodes.

45. The sensor of claim 35, wherein the first, second and third electrodes are coupled to a potentiostat for controlling and detecting the electrochemical reaction.

46. The sensor of claim 44, wherein the first, second and third electrodes are either inserted in the electrolyte or disposed on the substrate.

47. The sensor of claim 35, wherein the first electrode is a thin ITO (Indium-Tin-Oxide) film coated on a transparent substrate.

48. The sensor of claim 35, wherein the first electrode is a thin metal or carbon film deposited on the substrate.

49. The sensor of claim 35, wherein the first electrode comprises interconnected conductive lines deposited on the substrate.

50. The sensor of claim 35, wherein the optical system comprises an optical detector and a light source.

51. The sensor of claim 35, wherein the light source comprises ambient light, a light emitting diode or a laser diode.

52. The sensor of claim 35, wherein the optical system comprises an imaging or video system.

53. The sensor of claim 52, wherein the imaging or video system comprises a webcam, digital camera or charge-coupled device (CCD).

* * * * *